United States Patent [19]
Lohray et al.

[11] Patent Number: 6,159,966
[45] Date of Patent: Dec. 12, 2000

[54] AZOLIDINEDIONES USEFUL FOR THE TREATMENT OF DIABETES, DYSLIPIDEMIA AND HYPERTENSION: PROCESS FOR THEIR PREPARATION AND PHARMACEUTICAL COMPOSITIONS CONTAINING THEM

[75] Inventors: Braj Bhushan Lohray; Vidya Bhushan Lohray; Ashok Chennaveerappa Bajji; Shivaramayya Kalchar; Sekar Reddy Alla; Rajagopalan Ramanujam; Reeba Kannimel Vikramadithyan, all of Hyderabad, India

[73] Assignees: Reddy-Cheminor Inc., Ridgewood, N.J.; Dr. Reddy's Research Foundation, Hyderabad, India

[21] Appl. No.: 09/134,348

[22] Filed: Aug. 14, 1998

Related U.S. Application Data

[62] Division of application No. 08/982,910, Dec. 2, 1997.

[30] Foreign Application Priority Data

May 30, 1997 [IN] India .................... 1153/MAS

[51] Int. Cl.[7] .................. A61K 31/535; A61K 31/54; C07D 265/36; C07D 279/16
[52] U.S. Cl. .................. 514/224.8; 544/37; 544/38; 544/42; 544/43; 544/44; 544/45; 544/46; 544/102; 544/103; 544/104; 514/225.2; 514/225.5; 514/225.8; 514/226.2
[58] Field of Search .................. 544/37, 38, 42, 544/43, 44, 45, 46, 102, 103, 104; 514/225.2, 225.5, 225.8, 224.8, 226.2

[56] References Cited

U.S. PATENT DOCUMENTS

| | | | |
|---|---|---|---|
| 3,225,037 | 12/1965 | Zenitz et al. | 260/243 |
| 3,869,394 | 3/1975 | Daniels et al. | 252/46.7 |
| 3,912,727 | 10/1975 | Daniels | 260/243 |
| 4,873,255 | 10/1989 | Yoshioka | 514/369 |
| 5,002,953 | 3/1991 | Hindley | 514/275 |
| 5,037,842 | 8/1991 | Goldstein | 514/375 |
| 5,468,762 | 11/1995 | Malamas | 514/376 |
| 5,478,851 | 12/1995 | Cantello | 514/369 |
| 5,478,852 | 12/1995 | Olefsky | 514/369 |
| 5,478,853 | 12/1995 | Regnier | 514/369 |
| 5,521,201 | 5/1996 | Hindley | 514/342 |
| 5,955,481 | 9/1999 | Ohara et al. | 514/342 |

FOREIGN PATENT DOCUMENTS

| | | |
|---|---|---|
| 0139421 | 5/1985 | European Pat. Off. . |
| 0604983 | 7/1994 | European Pat. Off. . |
| 0612743 | 8/1994 | European Pat. Off. . |
| 0745600 | 12/1996 | European Pat. Off. . |
| 0783888 | 7/1997 | European Pat. Off. . |
| 0787727 | 8/1997 | European Pat. Off. . |
| 0912575 | 1/1997 | Japan . |
| 9112003 | 8/1991 | WIPO . |
| 9207838 | 5/1992 | WIPO . |
| 9425026 | 11/1994 | WIPO . |
| 9507697 | 3/1995 | WIPO . |
| 9521608 | 8/1995 | WIPO . |
| 9526347 | 8/1995 | WIPO . |
| 9535108 | 12/1995 | WIPO . |
| 9605186 | 2/1996 | WIPO . |
| 9611196 | 4/1996 | WIPO . |
| 9626207 | 8/1996 | WIPO . |
| 99/19313 | 4/1999 | WIPO . |

OTHER PUBLICATIONS

Messier, C. et al., Behavioral Brain Research, 75 (1966) 1–11.
Sohda, T. et al., Chem Pharm Bull. 30, 10 (1982), 3580–3600.
Clark, et al. J. Med. Chem 34 (1991) 319–325.
Dow, R. L. et al., J. Med. Chem 34 (1991) 1538–1544.
Hulin, et al., J. Med. Chem 35 (1992) 1853–1864.
Sohda, T. et al., J. Med. Chem 35 (1992) 2617–2626.
Goldstein, et al., J. Med. Chem. 36 (1993) 2238–2240.
Cantello, et al., J. Med. Chem 37 (1994) 3977–3985.
English Translation of JP–A–0912575.
M. Modan, et al., J. Clin. Invest. (1985) vol. 75, pp. 809–817.
O. G. Kolterman, et al., J. Clin. Invest. (1981) vol. 68, pp. 957–969.

(List continued on next page.)

*Primary Examiner*—Mukund J. Shah
*Assistant Examiner*—Hong Liu
*Attorney, Agent, or Firm*—Ladas & Parry

[57] ABSTRACT

A compound of formula (I)

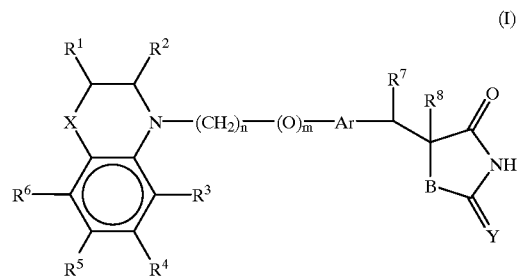

its tautomeric forms, its stereoisomers, its polymorphs, its pharmaceutically acceptable salts or its pharmaceutically acceptable solvates, wherein $R^3$, $R^4$, $R^5$, and $R^6$ are the same or different; $R^1$ and $R^2$ together represent along with carbon atoms to which they are attached an aromatic cyclic structure containing 5–6 ring atoms which may optionally be substituted; X represents a heteroatom selected from oxygen or sulfur; $R^7$ represents hydrogen atom, hydroxy, alkoxy, halogen, lower alkyl group or optionally substituted aralkyl group or forms a bond together with $R^8$; $R^8$ represents hydrogen atom, hydroxy, alkoxy, halogen, lower alkyl group or optionally substituted aralkyl or $R^8$ forms a bond together with $R^7$; B represents an oxygen atom or a sulfur atom; Y represents an oxygen atom or a sulfur atom, n is an integer ranging from 1 to 4 and m is an integer of zero or one, compositions containing compounds of formula (I) and methods of use of the compounds are described.

23 Claims, No Drawings

OTHER PUBLICATIONS

E. Ferrannini, et al., The New England Journal of Medicine (1987) vol. 317, pp. 350–357.

D.C. Shen, et al., J. Clin. Endocrinol. Metab. (1988) vol. 66, pp. 580–583.

Goodman & Gilman's The Pharmacological Basis of Therapeutics, Ninth Edition, pp. 1496–1497.

Clifford Bailey, "Potential New Treatments for Type 2 Diabetes", Chemistry & Industry, Jan. 19, 1998, pp. 53–57.

T. Antonucci, et al. "Imparied Glucose Tolerance is Normalized by Treatment with the Thiazolidinedione Troglitazone" Diabetes Care, vol. 20, No. 2, Feb. 1997, pp. 188–193.

AZOLIDINEDIONES USEFUL FOR THE TREATMENT OF DIABETES, DYSLIPIDEMIA AND HYPERTENSION: PROCESS FOR THEIR PREPARATION AND PHARMACEUTICAL COMPOSITIONS CONTAINING THEM

This is a divisional of U.S. patent application Ser. No. 08/982,910 filed on Dec. 2, 1997.

FIELD OF THE INVENTION

The present invention relates to novel antidiabetic compounds, their tautomeric forms, their derivatives, their analogues, their stereoisomers, their polymorphs, their pharmaceutically acceptable salts, their pharmaceutically acceptable solvates and pharmaceutically acceptable compositions containing them. This invention particularly relates to novel azolidinedione of the general formula (I), their derivatives, their analogues, their tautomeric forms, their stereoisomers, their polymorphs and their pharmaceutically acceptable salts, pharmaceutically acceptable solvates and pharmaceutical compositions containing them.

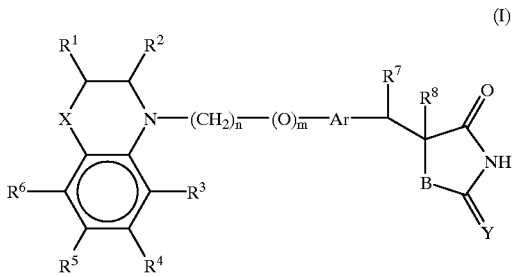

(I)

The present invention also relates to a process for the preparation of the above said novel azolidinedione compounds, their analogues, their derivatives, their tautomeric forms, their stereoisomers, their polymorphs, their pharmaceutically acceptable salts, pharmaceutically acceptable solvates, and pharmaceutical compositions containing them.

This invention also relates to novel intermediates, processes for preparing the intermediates and processes for using the intermediates.

The azolidinediones of the general formula (I) defined above of the present invention are useful for the treatment and/or prophylaxis of hyperlipemia, hypercholesteremia, hyperglycemia, osteoporosis, obesity, glucose intolerance, insulin resistance and also diseases or conditions in which insulin resistance is the underlying pathophysiological mechanism. Examples of these diseases and conditions are type II diabetes, impaired glucose tolerance, dyslipidaemia, hypertension, coronary heart disease and other cardiovascular disorders including atherosclerosis. The azolidinediones of the formula (I) are useful for the treatment of insulin resistance associated with obesity and psoriasis. The azolidinediones of the formula (I) can also be used to treat diabetic complications and can be used for treatment and/or prophylaxis of other diseases and conditions such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

BACKGROUND OF THE INVENTION

Insulin resistance is the diminished ability of insulin to exert its biological action across a broad range of concentrations. In insulin resistance, the body secretes abnormally high amounts of insulin to compensate for this defect; failing which, the plasma glucose concentration inevitably rises and develops into diabetes. Among the developed countries, diabetes mellitus is a common problem and is associated with a variety of abnormalities including obesity, hypertension, hyperlipidemia (J. Clin. Invest., (1985) 75: 809–817; N. Engl. J. Med. (1987) 317: 350–357; J. Clin. Endocrinol. Metab., (1988) 66: 580–583; J. Clin. Invest., (1975) 68: 957–969) and other renal complications (See Patent Application No. WO 95/21608). It is now increasingly being recognized that insulin resistance and relative hyperinsulinemia have a contributory role in obesity, hypertension, atherosclerosis and type 2 diabetes mellitus. The association of insulin resistance with obesity, hypertension and angina has been described as a syndrome having insulin resistance as the central pathogenic link-Syndrome-X. In addition, polycystic ovarian syndrome (Patent Application No. WO 95/07697), psoriasis (Patent Application No. WO 95/35108), dementia (Behavioral Brain Research (1996) 75: 1–11) etc. may also have insulin resistance as a central pathogenic feature. Recently, it has also been reported that thiazolidinediones improve the bone mineral density and thus may be useful for the treatment of osteoporosis (EP-783888).

A number of molecular defects have been associated with insulin resistance. These include reduced expression of insulin receptors on the plasma membrane of insulin responsive cells and alterations in the signal transduction pathways that become activated after insulin binds to its receptor including glucose transport and glycogen synthesis.

Since defective insulin action is thought to be more important than failure of insulin secretion in the development of non-insulin dependent diabetes mellitus and other related complications, this raises doubts about the intrinsic suitability of antidiabetic treatment that is based entirely upon stimulation of insulin release. Recently, Takeda has developed a new class of compounds which are the derivatives of 5-(4-alkoxybenzyl)-2,4-thiazolidinediones of the formula (II) (Ref. Chem. Pharm. Bull. 1982, 30, 3580–3600). In the formula (II), V represents substituted or unsubstituted divalent aromatic group, B represents a sulfur or an oxygen atom and U represents various groups which have been reported in various patent documents.

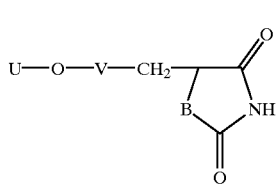

(II)

By way of examples, U may represent the following groups:
(i) a group of the formula (IIa) where $R^1$ is hydrogen or hydrocarbon residue or heterocyclic residue which may each be substituted, $R^2$ is hydrogen or a lower alkyl which may be substituted by hydroxy group, X is an oxygen or sulphur atom, Z is a hydroxylated methylene or a carbonyl, m is 0 or 1, n is an integer of 1–3. These compounds have been disclosed in the European Patent Application No. 0 177 353

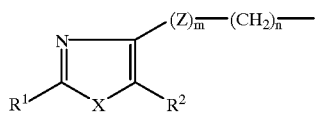
(IIa)

An Example of these compounds is shown in formula (IIb)

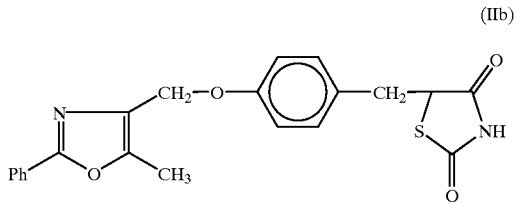
(IIb)

(ii) a group of the formula (IIc) wherein $R^1$ and $R^2$ are the same or different and each represents hydrogen or $C_1-C_5$ alkyl, $R^3$ represents hydrogen, acyl group, a $(C_1-C_6)$ alkoxycarbonyl group or aralkyloxycarbonyl group, $R^4-R^5$ are same or different and each represent hydrogen, $C_1-C_5$ alkyl or $C_1-C_5$ alkoxy or $R^4$, $R^5$ together represent $C_1-C_4$ alkenedioxy group, n is 1, 2, or 3, W represents $CH_2$, CO, $CHOR^6$ group in which $R^6$ represents any one of the items or groups defined for $R^3$ and may be the same or different from $R^3$. These compounds are disclosed in the European Patent Application No. 0 139 421.

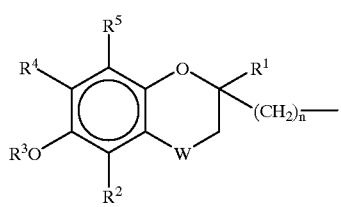
(IIc)

An example of these compounds is shown in (IId)

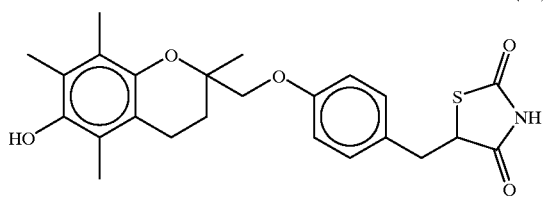
(IId)

iii) A group of formula (IIe) where $A^1$ represents substituted or unsubstituted aromatic heterocyclic group, $R^1$ represents a hydrogen atom, alkyl group, acyl group, an aralkyl group wherein the aryl moiety may be substituted or unsubstituted, or a substituted or unsubstituted aryl group, n represents an integer in the range from 2 to 6. These compounds are disclosed in European Patent No. 0 306 228.

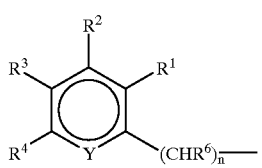
(IIe)

An example of this compound is shown in formula (IIf)

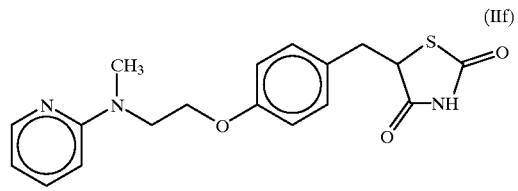
(IIf)

iv) A group of formula (IIg) where Y represents N or $CR^5$, $R^1$, $R^2$, $R^3$, $R^4$ and $R^5$ represents hydrogen, halogen, alkyl and the like and $R^6$ represents hydrogen, alkyl, aryl and the like, n represents an integer of 0 to 3. These compounds are disclosed in European Patent Application No. 0 604 983.

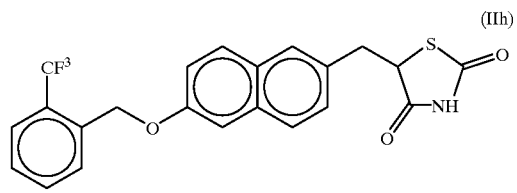
(IIg)

An example of this compound is shown in formula (IIh)

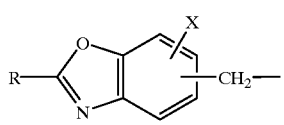
(IIh)

v) a group of formula (II i), where R is $(C_1-C_6)$ alkyl groups, cycloalkyl group, furyl, thienyl, substituted or unsubstituted phenyl group, X is hydrogen, methyl, methoxy, chloro or fluoro. These compounds have been disclosed in the U.S. Pat. No. 5,037,842.

(II i)

An example of these compounds is

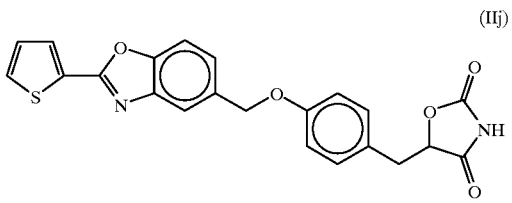

(IIj)

(vii) A group of formula (IIk) wherein A represents a substituted or unsubstituted aromatic heterocyclyl group; $R^1$ represents a hydrogen atom, an alkyl group, an acyl group, an aralkyl group, wherein the aryl moiety may be substituted or unsubstituted or a substituted or unsubstituted aryl group, n represents an integer in the range of from 2 to 6. These compounds have been disclosed in the patent application No. WO 92/02520.

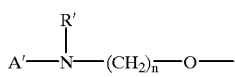

(IIk)

An example of these compounds is shown in formula (II l).

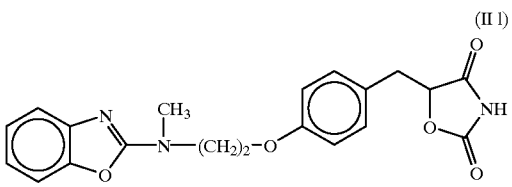

(II l)

SUMMARY OF THE INVENTION

With an objective of developing new compounds for the treatment of type II diabetes [non-insulin-dependent-diabetes mellitus (NIDDM)] which could be more potent at relatively lower doses and having better efficacy with lower toxicity, we focused our research efforts in a direction of incorporating safety and to have better efficacy, which has resulted in the development of novel azolidinedione compounds having the general formula (I) as defined above.

The main objective of the present invention is therefore, to provide novel azolidinedione compounds, their analogues, their derivatives, their tautomeric forms, their stereoisomers, their polymorphs, their pharmaceutically acceptable salts, their pharmaceutically acceptable solvates and pharmaceutical compositions containing them, or mixtures thereof.

Another objective of the present invention is to provide novel azolidinedione compounds, their analogues, their derivatives, their tautomeric forms, their stereoisomers, their polymorphs, their pharmaceutically acceptable salts, their pharmaceutically acceptable solvates and pharmaceutical compositions containing them or mixtures thereof having enhanced activities, no toxic effect or reduced toxic effect.

Yet another objective of the present invention is to produce a process for the preparation of novel azolidinediones of the formula (I) as defined above, their tautomeric forms, their analogues, their derivatives, their stereoisomers, their polymorphs, their pharmaceutically acceptable salts and their pharmaceutically acceptable solvates.

Still another objective of the present invention is to provide pharmaceutical compositions containing compounds of the general formula (I), their analogues, their derivatives, their tautomers, their stereoisomers, their polymorphs, their pharmaceutically acceptable salts, their pharmaceutically acceptable solvates or mixtures thereof in combination with suitable carriers, solvents, excipients, diluents and other media normally employed in preparing such compositions.

Yet another objective of the present invention is to provide a novel intermediate of the formula (III)

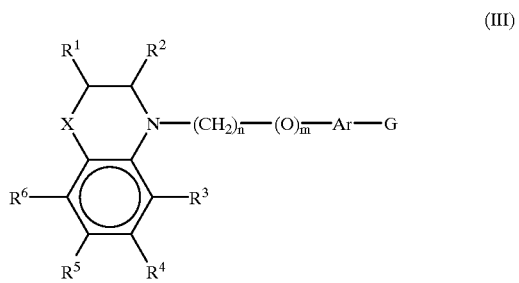

(III)

where G represents —CHO, —$NO_2$, —$NH_2$ or —$CH_2$—CH(J)—COOR, where J represents halogen atom such as chlorine, bromine or iodine and R represents H or lower alkyl group such as a ($C_1$–$C_6$) alkyl, preferably ($C_1$–$C_3$) alkyl, more preferably methyl, ethyl or propyl; and $R^1$–$R^6$, n, m and Ar are as defined in formula (I) and a process for the preparation thereof.

DETAILED DESCRIPTION OF THE INVENTION

Azolidinediones of the present invention have the general formula (I)

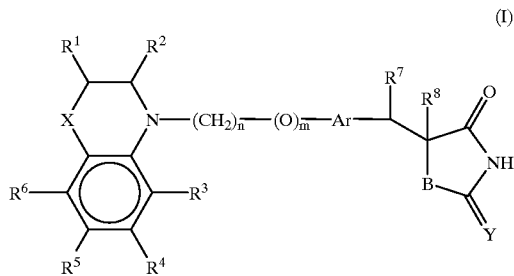

(I)

In the above formula, $R^1$, $R^2$, $R^3$, $R^4$, $R^5$, and $R^6$ may be same or different and represent hydrogen, halogen, hydroxy, cyano, nitro or optionally substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkoxycarbonyl, alkylamino, alkoxyalkyl, aryloxyalkyl, alkylmercapto, aralkoxycarbonylamino, alkoxycarbonylamino, aryloxycarbonylamino, mercaptoalkyl groups, carboxylic acid or its derivatives, or sulfonic acid or its derivatives; $R^1$ and $R^2$ may also together represent, along with carbon atoms to which they are attached an aromatic cyclic structure containing 5–6 ring atoms which may optionally be substituted; X represents a heteroatom selected from oxygen, sulfur or $NR^9$ where $R^9$ is hydrogen, alkyl, aryl, aralkyl, acyl, alkoxycarbonyl, aryloxycarbonyl, aralkoxycarbonyl and the like wherein these groups are defined as for $R^1$–$R^6$; Ar represents an optionally substituted divalent single or fused aromatic or heterocyclic group, $R^7$ represents hydrogen atom, hydroxy, alkoxy, halogen or lower alkyl such as $(C_1$–$C_6)$ alkyl such as methyl, ethyl, propyl and the like, optionally substituted aralkyl group or forms a bond together with the adjacent group $R^8$; $R^8$ represents hydrogen, hydroxy, alkoxy, halogen or lower alkyl group such as $(C_1$–$C_6)$ alkyl such as methyl, ethyl, propyl and the like, optionally substituted aralkyl or $R^8$ forms a bond together with $R^7$; B represents an oxygen atom or a sulfur atom; Y represents an oxygen atom or a sulfur atom, n is an integer ranging from 1 to 4 and m is an integer of zero or one.

Suitable groups represented by $R^1$–$R^6$ include hydrogen, halogen atom such as fluorine, chlorine, bromine, or iodine; hydroxy, cyano, nitro; substituted or unsubstituted $(C_1$–$C_{12})$ alkyl group, especially, linear or branched $(C_1$–$C_6)$alkyl group, such as methyl, ethyl, n-propyl, isopropyl, n-butyl, iso-butyl, t-butyl, n-pentyl, isopentyl, hexyl and the like; cycloalkyl group such as cyclopropyl, cyclobutyl, cyclopentyl, cyclohexyl and the like, the cycloalkyl group may be substituted; cycloalkyloxy group such as cyclopropyloxy, cyclobutyloxy, cyclopentyloxy, cyclohexyloxy and the like, the cycloalkoxy group may be substituted; aryl group such as phenyl or naphthyl, the aryl group may be substituted; aralkyl such as benzyl or phenethyl, $C_6H_5CH_2CH_2CH_2$, naphthylmethyl and the like, the aralkyl group may be substituted and the substituted aralkyl is a group such as $CH_3C_6H_4CH_2$, Hal—$C_6H_4CH_2$, $CH_3OC_6H_4$, $CH_3OC_6H_4CH_2CH_2$ and the like; heteroaryl group such as pyridyl, thienyl, furyl, pyrrolyl, oxazolyl, thiazolyl, imidazolyl, oxadiazolyl, tetrazolyl, benzopyranyl, benzofuranyl and the like, the heteroaryl group may be substituted; heterocyclyl groups such as aziridinyl, pyrrolidinyl, morpholinyl, piperidinyl, piperazinyl and the like, the heterocyclyl group may be substituted; aralkoxy group such as benzyloxy, phenethyloxy, naphthylmethyloxy, phenylpropyloxy and the like; heteroaralkyl group such as furanmethyl, pyridinemethyl, oxazolemethyl, oxazolethyl and the like; aralkylamino group such as $C_6H_5CH_2NH$, $C_6H_5CH_2CH_2NH$, $C_6H_5CH_2NCH_3$ and the like; aralkoxycarbonyl group such as benzyloxycarbonyl, phenethyloxycarbonyl, naphthylmethoxycarbonyl and the like; alkylamino group such as $NHCH_3$, $N(CH_3)_2$, $NCH_3(C_2H_5)$, $NHC_2H_5$ and the like; alkoxyalkyl group such as methoxymethyl, ethoxymethyl, methoxyethyl, ethoxyethyl and the like; aryloxyalkyl group such as $C_6H_5OCH_2$, $C_6H_5OCH_2CH_2$, naphthyloxymethyl and the like; heteroaryloxy and heteroaralkoxy, wherein heteroaryl moiety is as defined earlier and may be substituted; aryloxy group such as phenoxy, naphthyloxy, the aryloxy group may be substituted; alkoxycarbonyl such as methoxycarbonyl or ethoxycarbonyl; aryloxycarbonyl group such as optionally substituted phenoxycarbonyl, naphthyloxycarbonyl and the like; arylamino group such as $HNC_6H_5$; $NCH_3(C_6H_5)$—$NHC_6H_4CH_3$; —$NHC_6H_4$—Hal and the like; amino group; amino$(C_1$–$C_6)$alkyl; hydroxy$(C_1$–$C_6)$alkyl; $(C_1$–$C_6)$alkoxy; thio$(C_1$–$C_6)$alkyl; $(C_1$–$C_6)$alkylthio; acyl group such as acetyl, propionyl or benzoyl, the acyl group may be substituted; acylamino groups such as $NHCOCH_3$, $NHCOC_2H_5$, $NHCOC_3H_7$, $NHCOC_6H_5$, aralkoxycarbonylamino group such as $NHCOOCH_2C_6H_5$, —$NHCOOCH_2CH_2C_6H_5$, —$NCH_3COOCH_2C_6H_5$, —$NC_2H_5COOCH_2C_6H_5$, —$NHCOOCH_2C_6H_4CH_3$, —$NHCOOCH_2C_6H_4OCH_3$ and the like; aryloxycarbonylamino such as $NHCOOC_6H_5$, $NCH_3COOC_6H_5$, —$NC_2H_5COOC_6H_5$, —$NHCOOC_6H_4CH_3$, —$NHCOOC_6H_4OCH_3$ and the like; alkoxycarbonyl amino group such as $NHCOOC_2H_5$, $NHCOOCH_3$ and the like; carboxylic acid or its derivatives such as amides, like $CONH_2$, $CONHMe$, $CONMe_2$, $CONHEt$, $CONEt_2$, $CONHPh$ and the like, the carboxylic acid derivatives may be substituted; acyloxy group such as $OOCMe$, $OOCEt$, $OOCPh$ and the like which may optionally be substituted; sulfonic acid or its derivatives such as $SO_2NH_2$, $SO_2NHMe$, $SO_2NMe_2$, $SO_2NHCF_3$ and the like; the sulfonic acid derivatives may be substituted.

All the groups represented by $R^1$–$R^6$ may be substituted and the substituents may be selected from the same groups represented by $R^1$–$R^6$ and are defined in the same way.

Suitable cyclic structure formed by $R^1$, $R^2$ together with carbon atoms to which they are attached contain 5 to 6 ring atoms, preferably, optionally substituted phenyl, pyridyl, furanyl, thienyl, pyrrolyl, and the like; substituents may be selected from the same groups represented by $R^1$–$R^6$ and are defined in the same way. Preferred substituents are halogen, $(C_1$–$C_6)$alkoxy, cyclo$(C_3$–$C_6)$ alkyl, cyclo$(C_3$–$C_6)$alkoxy, aryl, aralkyl, aralkoxy, heterocyclyl, hydroxy, acyl, acyloxy, carboxyl, alkoxycarbonyl, aralkoxycarbonyl, amino, alkylamino, acylamino, aralkoxycarbonylamino, aminocarbonyl and the like.

Suitable X includes oxygen, sulfur or a group $NR^9$ as defined above. X is preferably oxygen or sulfur.

The group represented by Ar includes substituted or unsubstituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl, pyrazolyl and the like. The substituents on the group represented by Ar include linear or branched optionally halogenated $(C_1$–$C_6)$alkyl, optionally halogenated $(C_1$–$C_3)$ alkoxy, halogen, acyl, amino, acylamino, thio, carboxylic and sulfonic acids and their derivatives. The substituents are defined as they are for $R^1$–$R^6$.

It is more preferred that Ar represents a substituted or unsubstituted divalent phenylene, naphthylene, benzofuranyl, indolyl, indolinyl, quinolinyl, azaindolyl, azaindolinyl, benzothiazolyl or benzoxazolyl group.

It is still more preferred that Ar represents a divalent phenylene or benzofuranyl, which may be optionally substituted by methyl, halomethyl, methoxy or halomethoxy groups.

Suitable $R^7$ includes hydrogen, lower alkyl groups such as methyl, ethyl or propyl; hydroxy; $(C_1$–$C_3)$alkoxy; halogen atom such as fluorine, chlorine, bromine, or iodine; aralkyl such as $C_6H_5CH_2$, $C_6H_5CH_2CH_2$, $C_6H_5CH_2CH_2CH_2$, naphtylmethyl and the like, substituted aralkyl such as $CH_3C_6H_4CH_2$, Hal—$C_6H_4CH_2$, $CH_3OC_6H_4CH_2$, $CH_3OC_6H_4CH_2CH_2$ and the like, or $R^7$ together with $R^8$ represents a bond.

Suitable $R^8$ may be a hydrogen atom, hydroxy, $(C_1$–$C_3)$ alkoxy; halogen selected from fluorine, bromine, iodine and chlorine, lower alkyl group such as $(C_1$–$C_{12})$ alkyl, aralkyl such as $C_6H_5CH_2$, $C_6H_5CH_2CH_2$, $C_6H_5CH_2CH_2CH_2$, naphtylmethyl and the like, substituted aralkyl such as $CH_3C_6H_4CH_2$, Hal—$C_6H_4CH_2$, $CH_3OC_6H_4CH_2$, $CH_3OC_6H_4CH_2CH_2$ and the like, or together with $R^7$ forms a bond.

It is preferred that $R^7$ and $R^8$ represent hydrogen atoms or $R^7$ and $R^8$ together represent a bond.

Suitable B group includes a hetero atom selected from O or S, preferably sulfur atom.

Suitable ring structure comprising B and Y include 2,4-dioxooxazolidin-5-yl, 2,4-dioxothiazolidin-5-yl, 4-oxazolidine-2-thione-5-yl groups. Preferred ring structures comprising B include 2,4-dioxooxazolidin-5-yl and 2,4-dioxothiazolidin-5-yl groups.

It is more preferred that the ring structure comprising B is a 2,4-dioxothiazolidin-5-yl group.

Suitable Y group is a heteroatom selected from O or S.

Suitable m is an integer ranging from 0–1. It is preferred that when m=0, the linker group $(CH_2)_n$— is attached to the carbon atom adjacent to the heteroatom of the group Ar which represents an optionally substituted divalent benzofuranyl, benzoxazolyl, benzothiazolyl, indolyl, indolinyl, dihydrobenzofuryl, or dihydrobenzopyranyl group and when m=1, Ar represents substituted or unsubstituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl, pyrazolyl.

Suitable n is an integer ranging from 1 to 4, preferably n represents an integer 1 or 2.

It is preferred that when m=1, n represents 2.

It is also preferred that when m=0, n represents 1.

It is also preferred that when n represents 2 and m represents 1, that Ar represents phenyl or naphthyl groups.

Pharmaceutically acceptable salts forming part of this invention include salts of the azolidinedione moiety such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts, salts of carboxy group wherever appropriate, such as aluminum, alkali metal salts, alkaline earth metal salts, ammonium or substituted ammonium salts. Salts may include acid addition salts which are, sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. Pharmaceutically acceptable solvates may be hydrates or comprising other solvents of crystallization such as alcohols.

Particularly useful compounds according to the invention include:

5-[4-[2-(2,3-Dihydro-1,4-benzoxazin-4-yl)ethoxy]phenyl methylene]thiazolidine-2,4-dione;
5-[4-[2-(2,3-Dihydro-1,4-benzoxazin-4-yl)ethoxy]phenyl methyl]thiazolidine-2,4-dione;
5-[4-[2-(2,3-Dihydro-1,4-benzoxazin-4-yl)ethoxy]phenyl methyl]thiazolidine-2,4-dione, sodium salt;
5-[4-[2-(2,3-Dihydro-1,4-benzothiazin-4-yl)ethoxy]phenyl methyl]thiazolidine-2,4-dione;
5-[4-[2-(2,3-Dihydro-1,4-benzothiazin-4-yl)ethoxy]phenyl methyl]thiazolidine-2,4-dione;
5-[4-[2-(2,3-Dihydro-1,4-benzothiazin-4-yl)ethoxy]phenyl methyl]thiazolidine-2,4-dione, sodium salt;
5-[4-[2-(Phenoxazin-10-yl)ethoxy]phenyl methylene] thiazolidine-2,4-dione;
5-[4-[2-(Phenoxazin-10-yl)ethoxy]phenyl methyl] thiazolidine-2,4-dione;
5-[4-[2-(Phenoxazin-10-yl)ethoxy]phenyl methyl] thiazolidine-2,4-dione, sodium salt;
5-[2-[(2,3-Dihydro-1,4-benzoxazin-4-ylmethyl)benzofuran-5-yl]methylene]thiazolidine-2,4-dione;
5-[2-[(2,3-Dihydro-1,4-benzoxazin-4-ylmethyl)benzofuran-5-yl]methyl]thiazolidine-2,4-dione;
5-[2-[(2,3-Dihydro-1,4-benzoxazin-4-ylmethyl)benzofuran-5-yl]methyl]thiazolidine-2,4-dione; sodium salt;
5-[2-[(Phenothiazin-10-ylmethyl)-benzofuran-5-yl] methylene]thiazolidine-2,4-dione;
5-[2-[(Phenothiazin-10-ylmethyl)benzofuran-5-yl]methyl] thiazolidine-2,4-dione;
5-[4-[2-(Phenothiazin-10-yl)ethoxy]phenyl methylene] thiazolidine-2,4-dione;
5-[4-[2-(Phenothiazin-10-yl)ethoxy]phenyl methylene] thiazolidine-2,4-dione hydrochloride;
5-[4-[2-(Phenothiazin-10-yl)ethoxy]phenyl methyl] thiazolidine-2,4-dione;
5-[4-[2-(Phenothiazin-10-yl)ethoxy]phenyl methyl] thiazolidine-2,4-dione, hydrochloride;
5-[4-(2-(Phenothiazin-10-yl)ethoxy]phenyl methyl] thiazolidine-2,4-dione, sodium salt;
5-[4-[2-(Phenothiazin-10-yl)ethoxy]3-methoxyphenyl methylene]thiazolidine-2,4-dione;
5-[4-[2-(Phenothiazin-10-yl)ethoxy]-3-methoxyphenyl methyl]thiazolidine-2,4-dione;
5-[4-[2-[Phenoxazin-10-yl]ethoxy]phenyl methylene]-4-oxazolidinone-2-thione;
5-[4-(2-(9-Oxophenothiazin-10-yl)ethoxy]phenyl methylene]thiazolidine-2,4dione;
5-[4-[2-(9,9-Dioxophenothiazin-10-yl)ethoxy]phenyl methylene]thiazolidine-2,4-dione;
5-[4-[2-[2-Trifluoromethylphenothiazin-10-yl)ethoxy] phenyl methylene]thiazoldine-2,4-dione; and
5-[4-[2-[2-Trifluoromethylphenothiazin-10-yl]ethoxy] phenyl methyl]thiazolidine-2,4-dione.

According to a feature of the present invention, there is provided an intermediate of formula (III)

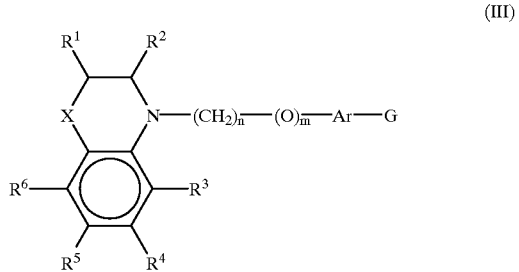

(III)

wherein G represents —CHO, —NO$_2$, —NH$_2$ or —CH$_2$CH(J)—COOR, where J represents halogen atom such as chlorine, bromine or iodine and R represents H or an alkyl group, preferably (C$_1$–C$_6$)alkyl group, more preferably (C$_1$–C$_3$) alkyl such as methyl, ethyl or propyl; R$^1$, R$^2$, R$^3$, R$^4$, R$^5$, and R$^6$ may be same or different and represent hydrogen, halogen, hydroxy, cyano, nitro or optionally substituted groups selected from alkyl, cycloalkyl, alkoxy, cycloalkoxy, aryl, aryloxy, aralkyl, aralkoxy, heterocyclyl, heteroaryl, heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkyloxycarbonyl, aralkoxycarbonylamino, alkoxycarbonylamino, aryloxycarbonylamino, alkylamino, alkoxyalkyl, aryloxyalkyl, alkylmercapto, mercaptoalkyl groups, carboxylic acid or its derivatives, or sulfonic acid or its derivatives; or R$^1$ and R$^2$ together may represent, along with carbon atoms to which they are attached an aromatic cyclic structure containing 5–6 ring atoms which may optionally be substituted; X represents a heteroatom selected from oxygen, sulfur or NR$^9$ where R$^9$ is hydrogen, alkyl, aryl, aralkyl, acyl, alkoxycarbonyl, aryloxycarbonyl, aralkoxycarbonyl and the like; Ar represents an optionally substituted divalent single or fused aromatic or heterocyclic group; n is an integer ranging from 1 to 4 and m is zero or 1.

According to another feature of the present invention, there is provided a process for the preparation of novel intermediate of the general formula (III)

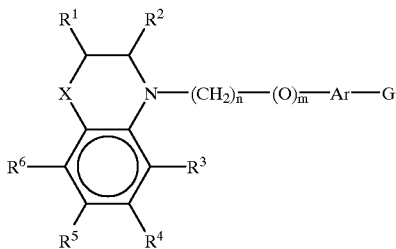 (III)

where $R^1-R^6$, Ar, X, n and m are as defined above and G represents a CHO or a $NO_2$ group or a group —$CH_2$—CH(J)—COOR, where J represents a halogen atom such as chlorine, bromine or iodine and R represents H or lower alkyl group as defined earlier.

In an embodiment of the invention, the novel intermediate of the general formula (III) defined above where G is CHO or $NO_2$ group and m=1, can be prepared by reacting the compound of the general formula (IV),

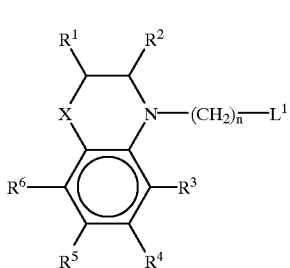 (IV)

wherein, $R^1-R^6$, X, n are as defined earlier and $L^1$ is a halogen atom such as chlorine, bromine or iodine or a leaving group such as methanesulfonate, trifluoromethanesulfonate, p-toluenesulfonate and the like with a compound of the formula (V)

 HO—Ar—G (V)

where G is a CHO or a $NO_2$ group and Ar is as defined earlier.

The reaction of compound of formula (IV) with the compound of formula (V) to produce a compound of formula (III) may be carried out in the presence of solvents such as THF, DMF, DMSO, DME and the like. Mixtures of solvents may be used. The inert atmosphere may be maintained by using inert gases such as $N_2$, Ar or He. The reaction may be effected in the presence of a base such as $K_2CO_3$, $Na_2CO_3$, NaH, or mixtures thereof. The reaction temperature may range from 20° C. to 150° C., preferably at a temperature in the range of 30° C. to 100° C. The duration of the reaction may range from 1 to 24 hours, preferably from 2 to 6 hours.

In another embodiment of the present invention, the novel intermediate of general formula (III), where G is a CHO or $NO_2$ group and m=1, can also be prepared by the reaction of compound of general formula (VI)

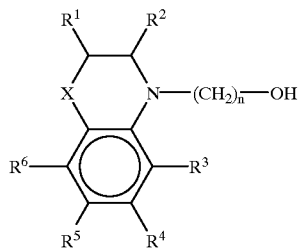 (VI)

where $R^1-R^6$, X and n are as defined earlier with a compound of general formula (VII)

 $L^2$—Ar—G (VII)

where G is a CHO or $NO_2$ group and Ar is as defined earlier and $L^2$ represents a halogen atom such as chlorine or fluorine.

The reaction of compound of formula (VI) with a compound of formula (VII) to produce a compound of the formula (III) may be carried out in the presence of solvents such as THF, DMF, DMSO, DME and the like or mixtures thereof. The reaction may be carried out in an inert atmosphere which may be maintained by using inert gases such as $N_2$, Ar, or He. The reaction may be effected in the presence of a base such as $K_2CO_3$, $Na_2CO_3$ or NaH or mixtures thereof. The reaction temperature may range from 20° C. to 120° C., preferably at a temperature in the range of 30° C. to 100° C. The duration of the reaction may range from 1 to 12 hours, preferably from 2 to 6 hours.

The novel intermediate of formula (III) defined above can also be obtained by the reaction of a compound of general formula (VI) defined above with a compound of general formula (V) defined earlier.

The reaction of compound of general formula (VI) with a compound of general formula (V) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, or He. The reaction may be effected in the presence of DMAP, HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of this invention, there is provided a process for the preparation of a compound of general formula (III) where G is a CHO or a $NO_2$ group, m is an integer of zero or one, and other symbols are as defined earlier which comprises reacting a compound of general formula (VIII)

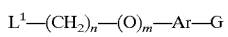 $L^1$—$(CH_2)_n$—$(O)_m$—Ar—G (VIII)

Were $L^1$, n, m, Ar and G are as defined earlier, with a compound of general formula (IX).

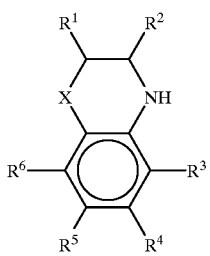

where $R^1$–$R^6$ and X are as defined earlier.

The reaction of compound of general formula (VIII) with a compound of general formula (IX) may be carried out neat or in the presence of solvents such as DMF, DMSO, $CH_3CN$, EtOH, acetone or mixtures thereof. The inert atmosphere may be maintained by using inert gases such as $N_2$, Ar, or He. The reaction may be effected in the presence of base such as $K_2CO_3$, $Na_2CO_3$, KOH, NaOH, NaH and the like or mixtures thereof. The amount of base may range from 1 to 20 equivalents, preferably 1 to 10 equivalents. The reaction may be carried out at a temperature in the range 20° C. to 180° C., preferably at a temperature in the range 50° C. to 150° C. Duration of the reaction may range from 1 to 48 hours, preferably from 1 to 12 hours. The amounts of the compound of general formula (VIII) and (IX) may range from 1 to 20 equivalents, preferably from 1 to 5 equivalents. The reaction may be carried out in the presence of phase transfer catalysts such as quaternary ammonium halides or hydroxides such as tetrabutyl ammonium bromide, tetrabutylammonium hydroxide, benzyl trimethylammonium bromide, aliquat and the like.

The present invention provides a process for the preparation of novel azolidinediones of general formula (I), their tautomeric forms, their derivatives, their analogues, their stereoisomers, their polymorphs, their pharmaceutically acceptable salts and their pharmaceutically acceptable solvates wherein $R^7$ and $R^8$ together represent a bond and B represents a sulfur or oxygen atom and all symbols are as defined earlier which comprises: reacting the compound of general formula (III), where G is a CHO group with 2,4-thiazolidinedione, 2,4-oxazolidinedione or oxazolidine-4-oxo-2-thione to yield a compound of general formula (X)

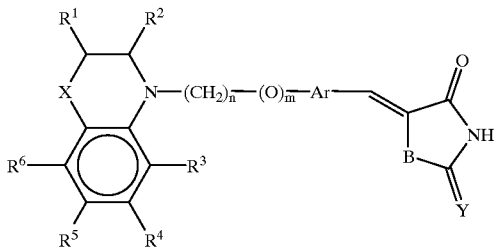

where $R^1$–$R^6$, X, Ar, n, m, B, and Y are as defined earlier, $R^7$ and $R^8$ together represent a bond and removing the water formed during the reaction by conventional methods.

The reaction of the compound of the general formula (III) where G is a CHO group with 2,4-thiazolidinedione or 2,4-oxazolidinedione to yield a compound of general formula (X) may be carried out neat in the presence of sodium acetate or in the presence of a solvent such as benzene, toluene, methoxyethanol or mixtures thereof. The reaction temperature may range from 80° C. to 140° C. depending upon the solvents employed and in the range from 80° C. to 180° C. when the reaction is carried out neat in the presence of sodium acetate. Suitable catalyst such as piperidinium acetate or benzoate, sodium acetate or mixtures of catalysts may also be employed. Sodium acetate can be used in the presence of solvent, but it is preferred that sodium acetate is used neat. The water produced in the reaction may be removed, for example, by using Dean Stark water separator or by using water absorbing agents like molecular seives. When oxazolidine-4-oxo-2-thione is used to produce a compound of formula (X), wherein B represents oxygen atom and Y represents sulfur atom, the thio group may be converted to oxo group by oxidation using agents such as hydrogen peroxide or peroxyacids like mCPBA.

The compound of the general formula (X) obtained in the manner described above is reduced by known method to obtain the compound of general formula (XI)

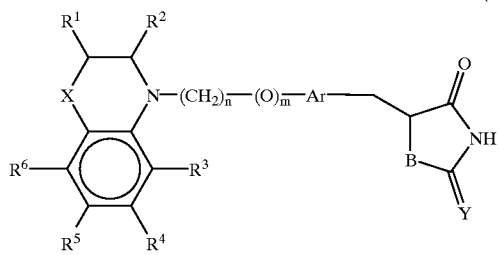

where $R^1$–$R^6$, X, Ar, n, m, B and Y are as defined earlier. The compound of general formula (XI) represents the compound of general formula (I), wherein $R^7$ and $R^8$ represent hydrogen atom and all other symbols are as defined earlier.

The reduction of compound of the formula (X) to yield a compound of the general formula (XI) may be carried out in the presence of gaseous hydrogen and a catalyst such as Pd/C, Rh/C, Pt/C, Raney Nickel, and the like. Mixtures of catalysts may be used. The reaction may be conducted in the presence of solvents such as dioxane, acetic acid, ethyl acetate and the like. Mixtures of solvents may be used. A pressure between atmospheric pressure and 80 psi may be employed. The catalyst may be 5–10% Pd/C and the amount of catalyst used may range from 50–50% w/w. The reaction may also be carried out by employing metal solvent reduction such as magnesium in methanol or sodium amalgam in methanol. The reaction may also be carried out with alkali metal borohydrides such as $LiBH_4$, $NaBH_4$, $KBH_4$ and the like, in the presence of cobalt salt such as $CoCl_2$ and ligands, preferably bidentated ligands such as 2,2'-bipyridyl, 1,10-phenanthroline, bisoximes and the like.

The compounds of general formula (X) and general formula (XI) obtained above may be converted into pharmaceutically acceptable salts, or pharmaceutically acceptable solvates by conventional methods.

In yet another embodiment of the present invention, the compound of the general formula (I) where m represents 1 and all other symbols are as defined earlier, can also be prepared by reacting a compound of the general formula (IV) defined above with a compound of general formula (XII)

(XII)

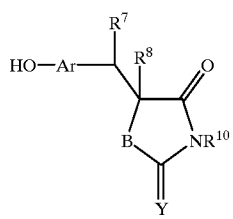

where $R^7$, $R^8$, B, Y and Ar are as defined earlier and $R^{10}$ is hydrogen or a nitrogen protecting group which is removed after the reaction.

The reaction of compound of general formula (IV) with a compound of general formula (XII) to produce a compound of general formula (I) may be carried out in the presence of solvents such as THF, DMF, DMSO, DME and the like or mixtures thereof. The reaction may be carried out in an inert atmosphere which may be maintained by using inert gases such as $N_2$, Ar or He. The reaction may be effected in the presence of a base such as alkalis like sodium hydroxide or potassium hydroxide; alkali metal carbonates like sodium carbonate or potassium carbonate; alkali metal hydrides such as sodium hydride; organometallic bases like n-butyl lithium; alkali metal amides like sodamide, or mixtures thereof. Multiple solvents and bases can be used. The amount of base may range from 1 to 5 equivalents, preferably 1 to 3 equivalents. The reaction temperature may be in the range of 0° C. to 120° C., preferably at a temperature in the range of 20° C. to 100° C. The duration of the reaction may range from 0.5 to 24 hours, preferably from 0.5 to 6 hours.

The removal of protecting groups may be carried out by conventional methods which include treatment with acid such as, hydrochloric acid, trifluoroacetic acid or bases such as, KOH, NaOH, $Na_2CO_3$, $NaHCO_3$, $K_2CO_3$ and the like or mixtures thereof. These reagents may be used as aqueous solution or as solutions in alcohols like methanol, ethanol etc. Deprotection can also be effected by gaseous hydrogen in the presence of catalyst such as Pd/carbon or conventional transfer hydrogenation methods when the protecting group is a benzyl or substituted benzyl group.

The compound of general formula (I) where m=1 and other symbols are as defined earlier, can also be obtained by reacting a compound of general formula (VI) with a compound of general formula (XII).

The reaction of compound of general formula (VI) with a compound of general formula (XII) to produce a compound of general formula (I) may be carried out using suitable coupling agents such as dicyclohexyl urea, triarylphosphine/dialkylazadicarboxylate such as $PPh_3$/DEAD and the like. The reaction may be carried out in the presence of solvents such as THF, DME, $CH_2Cl_2$, $CHCl_3$, toluene, acetonitrile, carbontetrachloride and the like. The inert atmosphere may be maintained by using inert gases such as $N_2$, Ar, He. The reaction may be effected in the presence of DMAP-HOBT and they may be used in the range of 0.05 to 2 equivalents, preferably 0.25 to 1 equivalents. The reaction temperature may be in the range of 0° C. to 100° C., preferably at a temperature in the range of 20° C. to 80° C. The duration of the reaction may range from 0.5 to 24 hours, preferably from 6 to 12 hours.

In another embodiment of the present invention, the compound of general formula (I), where $R^1$–$R^6$, X, n, m and Ar are as defined earlier and $R^7$ and $R^8$ represent hydrogen, B represents a sulfur atom and Y represents oxygen atom can be prepared by the reaction of compound of general formula (XIII)

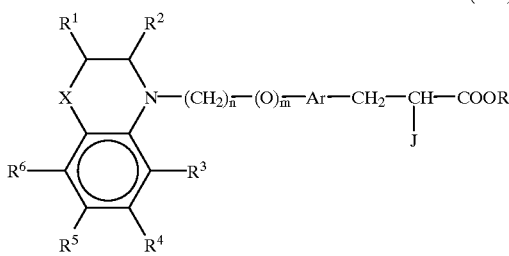

where $R^1$–$R^6$, X, Ar, m and n are as defined earlier, J is a halogen atom like chlorine, bromine or iodine and R is a lower alkyl group, with thiourea followed by treatment with an acid.

The reaction of compound of general formula (XIII) with thiourea is normally carried out in the presence of alcoholic solvent such as methanol, ethanol, propanol, isobutanol, 2-methoxybutanol, etc or DMSO or sulfolane. The reaction may be conducted at a temperature in the range between 20° C. and the reflux temperature of the solvent used. Bases such as NaOAc, KOAc, NaOMe, NaOEt etc. can be used. The reaction is normally followed by treatment with a mineral acid such as hydrochloric acid at 20° C. to 100° C.

The compound of general formula (XIII) where J is a halogen atom can be prepared by the diazotization of the amino compound of the general formula (XIV)

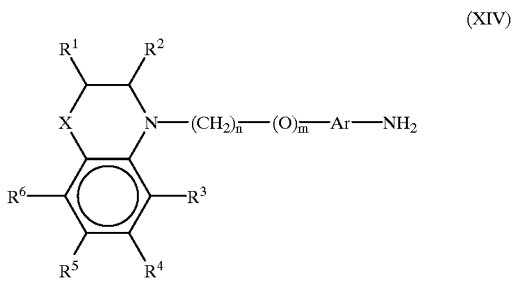

where all symbols are as defined earlier, using alkali metal nitrites followed by treatment with acrylic acid esters in the presence of hydrohalo acids and catalytic amount of copper oxide or copper halide.

The compound of general formula (XIV) can in turn be prepared by the conventional reduction of the novel intermediate (III) where G is $NO_2$ group and other symbols are as defined earlier.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases like lysine, arginine, diethanolamine, choline, guanidine and their derivatives etc. may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

As used in this application, the term neat means the reaction is carried out without the use of solvent.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, resolving the diastereomeric salts formed with chiral acids such as mandelic acid, camphorsulfonic acid, tartaric acid, lactic acid and the like or chiral bases such as brucine, cinchona alkaloids and their derivatives and the like.

Various polymorphs of the compounds of general formula (I) forming part of this invention may be prepared by crystallization of a compound of formula (I) under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or slow cooling. The presence of polymorphs may be determined by solid probe NMR spectroscopy, IR spectroscopy, differential scanning calorimetry, powder X-ray diffraction or such other techniques.

The present invention also provides a pharmaceutical composition, containing one or more of the compounds of the general formula (I) as defined above, their tautomeric forms, their derivatives, their analogues, their stereoisomers, their polymorphs, their pharmaceutically acceptable salts, their pharmaceutically acceptable solvates in combination with the usual pharmaceutically employed carriers, diluents and the like, useful for the treatment and/or prophylaxis of hyperlipemia, hypercholesteremia, hyperglycemia, osteoporosis, obesity, glucose intolerance, insulin resistance and also diseases in which insulin resistance is the underlying pathophysiological mechanism such as type II diabetes, impaired glucose tolerance, dyslipidaemia, hypertension, coronary heart disease and other cardiovascular disorders including atherosclerosis; insulin resistance associated with obesity and psoriasis, for treating diabetic complications and other diseases such as polycystic ovarian syndrome (PCOS), certain renal diseases including diabetic nephropathy, glomerulonephritis, glomerular sclerosis, nephrotic syndrome, hypertensive nephrosclerosis, end-stage renal diseases and microalbuminuria as well as certain eating disorders, as aldose reductase inhibitors and for improving cognitive functions in dementia.

The pharmaceutical composition may be in the forms normally employed, such as tablets, capsules, powders, syrups, solutions, suspensions and the like, may contain flavourants, sweeteners etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

A typical tablet production method is exemplified below:
Tablet Production Example

| a) | | |
|---|---|---|
| | 1) Active ingredient | 30 g |
| | 2) Lactose | 95 g |
| | 3) Cornstarch | 30 g |
| | 4) Carboxymethyl cellulose | 44 g |
| | 5) Magnesium stearate | 1 g |
| | | 200 g for 1000 tablets |

The ingredients 1 to 3 are uniformly blended with water and granulated after drying under reduced pressure. The ingredients 4 and 5 are mixed well with the granules and compressed by a tabletting machine to prepare 1000 tablets each containing 30 mg of active ingredient.

| b) | | |
|---|---|---|
| | 1) Active ingredient | 30 g |
| | 2) Calcium phosphate | 90 g |
| | 3) Lactose | 40 g |
| | 4) Corn starch | 35 g |
| | 5) Polyvinyl pyrrolidone | 3.5 g |
| | 6) Magnesium stearate | 1.5 g |
| | | 200 g for 1000 tablets |

The ingredients 1–4 are uniformly moistened with an aqueous solution of 5 and granulated after drying under reduced pressure. Ingredient 6 is added and granules are compressed by a tabletting machine to prepare 1000 tablets containing 30 mg of ingredient 1.

The compound of the formula (I) as defined above are clinically administered to mammals, including man, via either oral or parenteral routes. Administration by the oral route is preferred, being more convenient and avoiding the possible pain and irritation of injection. However, in circumstances where the patient cannot swallow the medication, or absorption following oral administration is impaired, as by disease or other abnormality, it is essential that the drug be administered parenterally. By either route, the dosage is in the range of about 0.10 mg to about 200 mg/kg body weight of the subject per day or preferably about 0.10 mg to about 50 mg/kg body weight per day administered singly or as a divided dose. However, the optimum dosage for the individual subject being treated will be determined by the person responsible for treatment, generally smaller doses being administered initially and thereafter increments made to determine the most suitable dosage.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

The invention is explained in detail in the examples given below which are provided by way of illustration only and therefore should not be construed to limit the scope of the invention.

Preparation 1

4-[2-(2,3-Dihydro-1,4-benzoxazin-4-yl)ethoxy] benzaldehyde

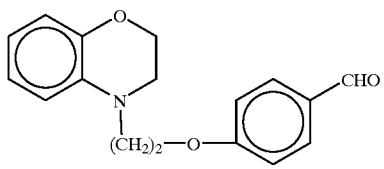

Step A

Preparation of 2-(2,3-dihydro-1,4-benzoxazine-4-yl) ethyl methanesulfonate

To a solution of 2-(2,3-dihydro-1,4-benzoxazin-4-yl) ethanol (17.0 g, 94.9 mmol) in pyridine (200 ml) was added methanesulfonyl chloride (16.31 g, 142.0 mmol) dropwise at 0° C. The reaction mixture was stirred for 10 h at 25° C. Ice water (200 ml) was added and the mixture was extracted with ethyl acetate (2×100 ml). The combined organic extracts were washed with 2N HCl (3×75 ml), water (75 ml), brine (50 ml) and dried ($Na_2SO_4$). The solvent was evaporated under reduced pressure. The residue was triturated with 5% ethyl acetate in pet. ether to afford the title compound (15.0 g, 61%) as brown solid. mp. 92–95° C.

$^1$H NMR ($CDCl_3$, 200 MHz): δ2.97 (s, 3H), 3.45 (t, J=4.43 Hz, 2H), 3.64 (t, J=5.72 Hz, 2H), 4.23 (t, J=4.21 Hz, 2H), 4.41 (t, J=5.71 Hz, 2H), 6.66 (m, 2H), 6.83 (m, 2H).

Step B

A mixture of 2-(2,3-dihydro-1,4-benzoxazin-4-yl)ethyl methanesulfonate (5 g, 19.4 mmol) obtained above, p-hydroxy benzaldehyde (5.56 g, 29.1 mmol) and potassium carbonate (10.75 g) in dry dimethyl formamide (50 ml) was heated to 70° C. for 7 h. The reaction mixture was cooled to room temperature. Water (100 ml) was added to the mixture and extracted with ethyl acetate (2×100 ml). The organic extracts were washed with water (50 ml), brine (50 ml) and dried ($Na_2SO_4$). The solvent was removed under reduced pressure to afford the title compound (4.0 g, 72%) as a syrupy liquid.

$^1$H NMR ($CDCl_3$, 200 MHz): δ3.55 (t, J=4.3 Hz, 2H), 3.76 (t, J=5.5 Hz, 2H), 4.26 (m, 4H), 6.74 (m, 2H), 6.83 (m, 2H), 7.02 (d, J=8.6 Hz, 2H), 7.85 (d, J=8.5 Hz, 2H), 9.90 (s, 1H).

Preparation 2

4-[2-(2,3-Dihydro-1,4-benzothiazin-4-yl)ethoxy] benzaldehyde

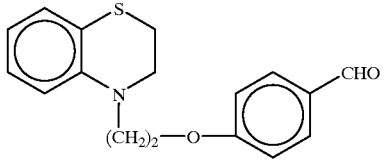

To a mixture of 4-hydroxy benzaldehyde (1.8 g, 14.8 mmol) and triphenyl phosphine (4.85 g, 18.5 mmol) in tetrahydrofuran (15 ml) was added 2-(2,3-dihydro-1,4-benzothiazin-4-yl)ethanol (2.39 g, 12.3 mmol) and diisopropyl azodicarboxylate (3.74 g, 18.5 mmol) in THF (20 ml) at 25° C. The reaction mixture was stirred for 12 h at 25° C. Water (100 ml) was added and the mixture was extracted with ethyl acetate (2×100 ml). The organic extracts were dried ($Na_2SO_4$) and solvent was evaporated under reduced pressure. The crude product was chromatographed over silica gel using a mixture of methanol and chloroform (5:95) as an eluent to afford the title compound (1.6 g, 44%) as an oil.

$^1$H NMR ($CDCl_3$, 200 MHz): δ3.05 (t, J=5.0 Hz, 2H), 3.80 (m, 4H), 4.26 (t, J=5.5 Hz, 2H), 6.68 (m, 2H), 7.03 (m, 4H), 7.83 (d, J=8.6 Hz, 2H), 9.88 (s, 1H).

Preparation 3

4-[2-(Phenoxazin-10-yl)ethoxy]benzaldehyde

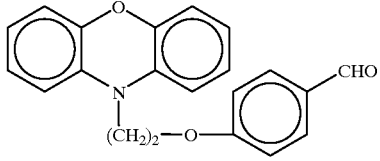

To a suspension of sodium hydride (60% mineral oil, 0.13 g, 3.24 mmol) in dimethyl formamide (3 ml) was added phenoxazine (0.5 g, 2.7 mmol) in dimethyl formamide (5 mL). The reaction mixture was stirred at 25° C. for 0.5 h and a solution of 4-(2-bromoethoxy)benzaldehyde (0.74 g, 3.24 mmol) in dimethyl formamide (3 mL) was added. The reaction mixture was stirred at 25° C. for 6 h. Water (25 ml) was added and the mixture was extracted with ethyl acetate (2×50 ml). The combined organic layers were washed with water (50 ml), brine solution (50 ml) and dried ($Na_2SO_4$). The solvent was evaporated and the residue was chromatographed over silica gel using a mixture of ethyl acetate and pet. ether (3:7) as eluent to afford the title compound (0.52 g, 57%) as a syrupy liquid.

$^1$H NMR ($CDCl_3$, 200 MHz): δ3.67 (t, J=6.2 Hz, 1H), 4.05 (t, J=6.2 Hz, 1H), 4.28 (t, J=6.3 Hz, 1H), 4.38 (t, J=6.2 Hz, 1H), 6.75 (m, 8H), 7.02 (m, 2H), 7.87 (m, 2H), 9.90 (s, 1H).

Preparation 4

4-[2-(Phenothiazin-10-yl)ethoxy]benzaldehyde

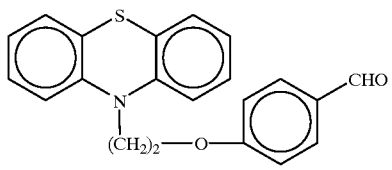

Step A 2-(phenothiazin-10-yl)ethyl methanesulfonate

To a solution of (phenothiazin-10-yl)ethanol (20.0 g, 82.0 mmol) in dichloromethane (150 ml) was added triethyl amine(24.9 g, 24 mmol) at 0° C. Methanesulfonyl chloride (18.8 g, 160 mmol) in dichloromethane (50 ml) was added dropwise to the above reaction mixture at 0° C. The reaction mixture was stirred for 3 h at 25° C. Ice water (250 ml) was added and organic layer was washed with 2 N HCl (2×50 ml), water (75 ml) and dried ($Na_2SO_4$). The solvent was evaporated under reduced pressure. The residue was triturated with pet. ether to afford the title compound (21 g, 80%) as a brown solid. mp. 96–97° C.

$^1$H NMR ($CDCl_3$, 200 MHz): δ2.93 (s, 3H), 4.28 (t, J=5.81 Hz, 2H), 4.52 (t, J=5.81 Hz, 2H), 6.91 (m, 4H), 7.20 (m, 4H).

Step B

The title compound (14.0 g, 59%) was prepared as a white solid from 2-(phenothiazin-10-yl)ethyl methanesulfonate (22.0 g, 68.8 mmol) obtained above, p-hydroxy benzaldehyde (10.0 g, 82.61 mmol) and potassium carbonate (19.0 g, 187.6 mmol) by an analogous procedure to that described in preparation 1. mp: 128–130° C.

$^1$H NMR ($CDCl_3$, 200 MHz): δ4.39 (s, 4H), 6.98 (m, 6H), 7.16 (m, 4H), 7.82 (d, J=7.2 Hz, 2H), 9.86 (s, 1H).

Preparation 5

5-Formyl-2-(2,3-dihydro-1,4-benzoxazin-4-ylmethyl)benzofuran

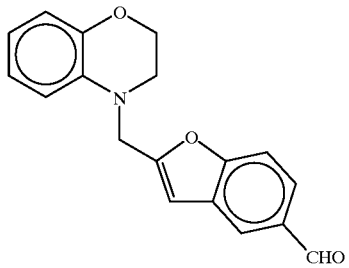

A mixture of 2,3-dihydro-1,4-benzoxazine (1.07 g, 7.94 mmol), 2-bromomethyl-5-formyl benzofuran (1.9 g, 7.94 mmol), potassium carbonate (5.5 g, 39.74 mmol) and Aliquat 336 (2 drops) in dimethyl formamide (25 ml) was stirred at 65° C. for 8 h. Water (50 ml) was added to reaction mixture and extracted with ethyl acetate (2×50 ml). The extracts were washed with water (50 ml), brine (50 ml) and dried ($Na_2SO_4$). The solvent was evaporated to dryness and the residue was chromatographed over silica gel using a mixture of ethyl acetate:pet. ether (3:7) as an eluent to afford the title compound (2.1 g, 91%) as an oil.

$^1$H NMR ($CDCl_3$, 200 MHz): δ3.39 (t, J=4.48 Hz, 2H), 4.28 (t, J=4.57 Hz, 2H), 4.56 (s, 2H), 6.80 (m, 5H), 7.52 (d, J=8.63 Hz, 1H), 7.81 (d, J=8.62 Hz, 1H), 8.01 (s, 1H), 10.0 (s, 1H).

Preparation 6

5-Formyl-2-(phenothiazin-10-ylmethyl)benzofuran

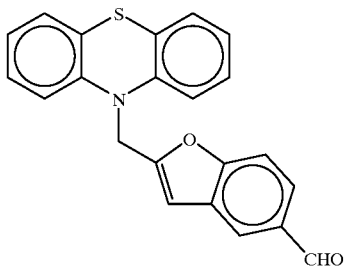

The title compound (1.14 g, 33%) was prepared as a syrupy liquid from phenothiazine (2.87 g, 14.0 mmol) and 2-bromomethyl-5-formyl benzofuran (2.3 g, 9.6 mmol) by a similar procedure to that described in preparation 5.

$^1$H NMR ($CDCl_3$, 200 MHz): δ5.20 (s, 2H), 6.98 (m, 9H), 7.65 (d, J=8.6 Hz, 1H), 7.89 (d, J=8.6 Hz, 1H), 8.01 (s, 1H), 10.09 (s, 1H).

Preparation 7

3-Methoxy-4-[2-(phenothiazin-10-yl)ethoxy]benzaldehyde

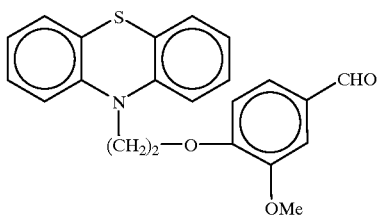

The title compound (2.5 g, 71%) was prepared as a white solid from 2-(phenothiazin-10-yl)ethyl methanesulfonate (3.0 g, 9.3 mmol) and vanillin (1.7 g, 11.2 mmol) using a similar procedure to that described in preparation 4. mp: 130° C.

$^1$H NMR ($CDCl_3$, 200 MHz): δ3.94 (s, 3H), 4.43 (s, 4H), 6.8–7.5 (complex, 11H), 9.84 (s, 1H).

Preparation 8

4-[2-(9-Oxophenothiazin-10-yl)ethoxy]benzaldehyde

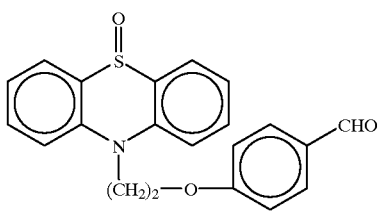

The title compound (2.2 g, 67%) was prepared as a thick liquid from 9-oxophenothiazin (2.0 g, 9.3 mmol) and 2-(4-formylphenoxy)ethyl methanesulfonate (2.7 g, 11 mmol) using a similar procedure to that described in preparation 3.

$^1$H NMR ($CDCl_3$, 200 MHz) δ: 4.52 (t, J=6.4 Hz, 2H), 4.75 (t, J=6.4 Hz, 2H), 7.0 (d J=8.6 Hz, 2H), 7.3 (m, 2H), 7.6 (m, 4H), 7.82 (d, J=8.6 Hz, 2H), 8.0 (m, 2H), 9.87 (s, 1H).

Preparation 9

4-[2-(9,9-Dioxophenothiazin-10-yl)ethoxy] benzaldehyde

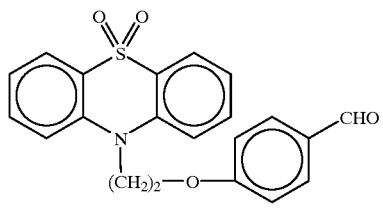

To a mixture of 4-[2-(phenothiazin-10-yl)ethoxy] benzaldehyde (0.25 g, 0.7 mmol) obtained in preparation 4 and 4-methyl morpholine N-oxide (0.16 g, 1.4 mmol) in acetone, osmium tetroxide (0.02 g, 0.07 mmol) was added and the mixture was stirred at room temperature for 3 h. At the end of this time, the reaction mixture was diluted with water and extracted with ethylacetate (50 ml). The ethylacetate layer was washed with aq. $NaHSO_3$ solution (25 ml), dried and concentrated to get (0.23 g, 65%) the title compound as a gummy liquid.

$^1$H NMR ($CDCl_3$, 200 MHz) δ: 4.47 (t, J=6.4 Hz, 2H), 4.7 (t, J=6.4 Hz, 2H), 7.0 (d, J=8.4 Hz, 2H), 7.3 (m, 2H), 7.47 (d, J=8.8 Hz, 2H), 7.66 (t, J=7.4 Hz, 2H), 7.83 (d, J=8.6 Hz, 2H), 8.15 (d, J=7.2 Hz, 2H), 9.89 (s, 1H).

Preparation 10

4-[2-[2-Trifluoromethylphenothiazin-10-yl]ethoxy] benzaldehyde

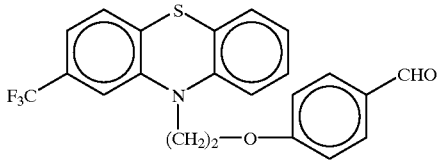

The title compound (1.0 g, 65%) was prepared as a thick liquid from 2-(trifluoromethyl)phenothiazine (1.0 g, 3.7 mmol) and 4-(2-bromoethoxy)benzaldehyde (1.6 g, 7.49 mmol) by a similar procedure to that described in preparation 3.

$^1$H NMR ($CDCl_3$, 200 MHz): δ4.39 (s, 4H), 7.0 (m, 4H), 7.2 (m, 5H), 7.82 (d, J=8.8 Hz, 2H), 9.88 (s, 1H).

EXAMPLE 1

5-[4-[2-(2,3-Dihydro-1,4-benzoxazin-4-yl)ethoxy] phenyl methylene]thiazolidine-2,4-dione

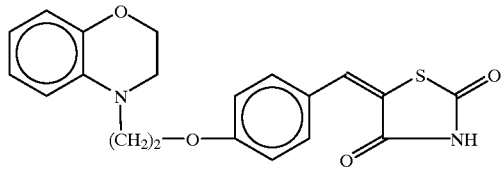

A solution of 4-[2-(2,3-dihydro-1,4-benzoxazin-4-yl) ethoxy]benzaldehyde (1.79 g, 6.36 mmol) obtained in preparation 1 and 2,4-thiazoldinedione (0.74 g, 6.36 mmol) in toluene (100 ml) containing piperidine (73 mg, 0.858 mmol) and benzoic acid (90 mg, 0.74 mmol) was heated under reflux for 3 h using Dean-Stark apparatus. The reaction mixture was cooled to room temperature, solid separated was filtered and washed with cold toluene (2×10 ml). The solid product was recrystallised from chloroform-methanol to afford the title compound (1.92 g, 79%) as a yellow solid. mp: 186–188° C.

$^1$H NMR (DMSO-$d_6$, 200 MHz): δ3.47 (bs, 2H), 3.69 (t, J=4.9 Hz, 2H), 4.13 (bs, 2H), 4.25 (t, J=4.9 Hz, 2H), 6.52 (m, 1H), 6.70 (m, 3H), 7.11 (d, J=8.3 Hz, 2H), 7.56 (d, J=8.3 Hz, 2H), 7.75 (s, 1H), 12.53 (s, 1H).

EXAMPLE 2

5-[4-[2-(2,3-Dihydro-1,4-benzoxazin-4-yl)ethoxy] phenyl methyl]thiazolidine-2,4-dione

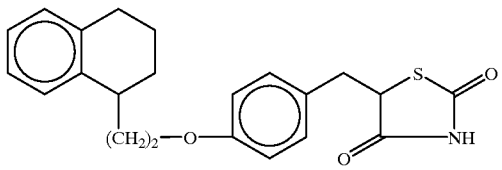

A mixture of 5-[4-[2-(2,3-Dihydro-1,4-benzoxazin-4-yl) ethoxy]phenyl-methylene]thiazolidine-2,4-dione (1.2 g, 3 mmol) obtained in example 1 and magnesium turnings (1.25 g, 51 mmol) in methanol (50 ml) was stirred at 25° C. for 20 h. At the end of this time water (50 ml) was added and pH was adjusted to 6.5–7.0 using 10% aqueous hydrochloric acid and the solution was extracted with ethyl acetate (2×75 ml). The combined organic extract was washed with water (50 ml), brine (50 ml), dried ($Na_2SO_4$) and the solvent was removed under reduced pressure. The residue was chromatographed over silica gel using a mixture of ethyl acetate and pet. ether (2:8) as an eluent to give (0.5 g, 41%) the title compound as a syrupy liquid.

$^1$H NMR ($CDCl_3$, 200 MHz): δ3.08 (dd, J=14.11 and 9.2 Hz, 1H), 3.47 (m, 3H), 3.66 (t, J=5.4 Hz, 2H), 4.15 (m, 4H), 4.40 (dd, J=9.2 and 3.9 Hz, 1H), 6.75 (m, 6H), 7.09 (d, J=8.6 Hz, 2H), 8.12 (bs, 1H, $D_2O$ exchangeable).

EXAMPLE 3

5-[4-[2-(2,3-Dihydro-1,4-benzoxazin-4-yl)ethoxy] phenyl methyl]thiazolidine-2,4-dione, sodium salt

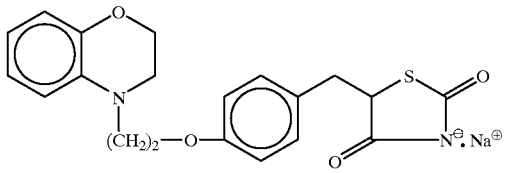

A mixture of 5-[4-[2-(2,3-dihydro-1,4-benzoxazin-4-yl) ethoxy]phenyl methyl]thiazolidine-2,4-dione (0.25 g, 0.651 mmol) obtained in example 2 and sodium methoxide (0.1 g, 1.95 mmol) in methanol (10 ml) was stirred at 25° C. for 14 h. The resulting solid was filtered, washed with methanol (2×5 ml), with ether (2×10 ml) and dried under vacuum at 70° C. to afford the title compound (0.23 g, 87%) as a white solid. mp: 265–267° C.

$^1$H NMR (DMSO-$d_6$, 200 MHz): δ2.53 (m, 1H), 3.32 (m, 1H), 3.47 (t, J=4.2 Hz, 2H), 3.67 (t, J=5.4 Hz, 2H), 4.15 (m, 5H), 6.55 (m, 1H), 6.82 (m, 5H), 7.12 (d, J=8.6 Hz, 2H).

EXAMPLE 4

5-[4-[2-(2,3-Dihydro-1,4-benzothiazin-4-yl)ethoxy]phenyl methylene]thiazolidine-2,4-dione

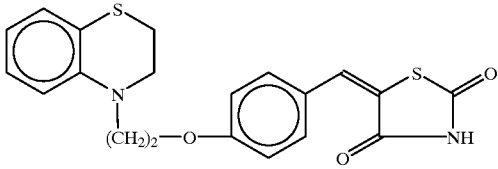

The title compound (1.7 g, 85%) was prepared as a yellow solid from 4-[2-(2,3-dihydro-1,4-benzothiazin-4-yl)ethoxy] benzaldehyde (1.5 g, 5.01 mmol), obtained in preparation 2 and 2,4-thiazolidinedione (0.65 g, 5.52 mmol), by a similar procedure to that described in example 1. mp: 214–217° C.

$^1$H NMR (CDCl$_3$, 200 MHz): δ3.04 (t, J=4.7 Hz, 2H), 3.70 (m, 4H), 4.24 (t, J=5.3 Hz, 2H), 6.58 (m, 1H), 6.90 (m, 3H), 7.12 (d, J=8.6 Hz, 2H), 7.54 (d, J=8.7 Hz, 2H), 7.75 (s, 1H), 12.53 (s, 1H, D$_2$O exchangeable).

EXAMPLE 5

5-[4-[2-(2,3-Dihydro-1,4-benzothiazin-4-yl]ethoxy]phenyl methyl]thiazolidine-2,4-dione

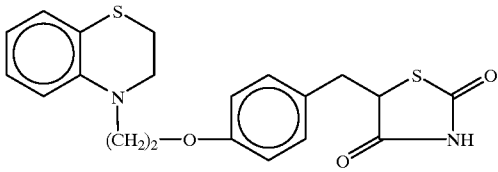

The title compound (0.5 g, 43%) was prepared as a syrupy liquid from 5-[4-[2-(2,3-dihydro-1,4-benzothiazin-4-yl)ethoxy]phenyl methyl]thiazolidine-2,4-dione obtained in example 4 by an analogous procedure to that described in example 2.

$^1$H NMR (CDCl$_3$, 200 MHz): δ3.12 (m, 3H), 3.44 (dd, J=14.2 and 3.7 Hz, 1H), 3.73 (m, 4H), 4.16 (t, J=5.8 Hz, 2H), 4.46 (m, 1H), 6.76 (m, 4H), 7.13 (m, 4H).

EXAMPLE 6

5-[4-[2-(2,3-Dihydro-1,4-benzothiazin-4-yl)ethoxy]phenyl methyl]thiazolidine-2,4-dione, sodium salt

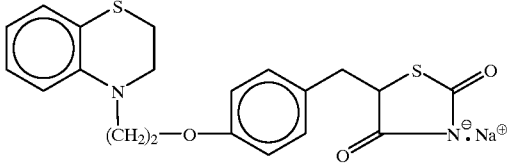

The title compound (0.23 g, 78%) was prepared as a white solid from 5-[4-[2-(2,3-dihydro-1,4-benzoxazin-4-yl)ethoxy]phenyl methyl]thiazolidine-2,4-dione obtained in example 5 by an analogous procedure to that described in example 3. mp: 261–265° C.

$^1$H NMR (DMSO-d$_6$, 200 MHz): δ2.60 (m, 1H), 3.02 (t, J=4.9 Hz, 2H), 3.29 (dd, J=14.5 and 3.9 Hz, 1H), 3.66 (m, 4H), 4.11 (m, 3H), 6.56 (m, 1H), 6.89 (m, 5H), 7.09 (d, J=8.5 Hz, 2H).

EXAMPLE 7

5-[4-[2-(Phenoxazin-10-yl)ethoxy]phenyl methylene]thiazolidine-2,4-dione

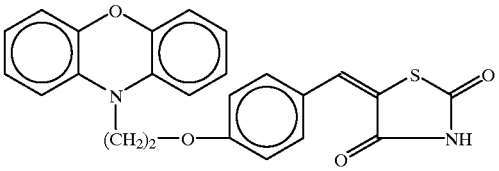

The title compound (1.46 g, 75%) was prepared as a pale yellow solid from 4-[2-(phenoxazin-10-yl)ethoxy] benzaldehyde (1.5 g, 4.5 mmol) obtained in preparation 3 and 2,4-thiazolidinedione (0.53 g, 4.5 mmol) by an analogous procedure to that described in example 1. mp: 204–206° C.

$^1$H NMR (DMSO-d$_6$, 200 MHz): δ4.04 (t, J=5.9 Hz, 2H), 4.26 (t, J=6.2 Hz, 2H), 6.65 (m, 8H), 6.99 (d, J=8.8 Hz, 2H), 7.43 (d, J=8.8 Hz, 2H), 7.72 (s, 1H), 11.89 (bs, 1H, D$_2$O exchangeable).

EXAMPLE 8

5-[4-[2-(Phenoxazin-10-yl)ethoxy]phenyl methyl]thiazolidine-2,4-dione

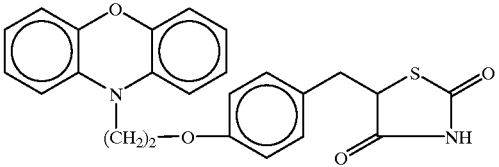

The title compound (0.72 g, 60%) was prepared as a white solid from 5-[4-[2-(phenoxazin-10-yl)ethoxy]phenyl methylene]thiazolidene-2,4-dione (1.2 g, 2.79 mmol) obtained in example 7, by an analogous procedure to that described in example 2. mp: 170–172° C.

$^1$H NMR (CDCl$_3$, 200 MHz): δ3.13 (dd, J=14.0 and 9.2 Hz, 1H), 3.44 (dd, J=14.0 and 3.7 Hz, 1H), 3.98 (t, J=6.3 Hz, 2H), 4.18 (t, J=6.2 Hz, 2H), 4.51 (dd, J=9.0 and 4.0 Hz, 1H), 6.65 (m, 6H), 6.86 (m, 4H), 7.15 (d, J=8.6 Hz, 2H), 8.15 (bs, 1H, D$_2$O exchangeable).

EXAMPLE 9

5-[4-[2-(Phenoxazin-10-yl)ethoxy]phenyl methyl]thiazolidine-2,4-dione sodium salt

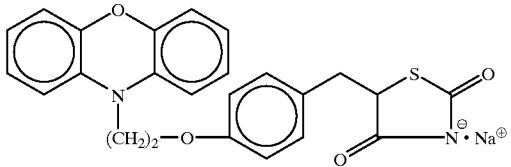

The title compound (0.06 g, 57%) was prepared as a white solid from 5-[4-[[2-(phenoxazin-10-yl)ethoxy]phenyl methyl]thiazolidine-2,4-dione (0.1 g, 0.2 mmol) obtained in example 8 by an analogous procedure to that described in example 3. mp: 260–262° C.

$^1$H NMR (DMSO-d$_6$, 200 MHz): δ2.59 (m, 1H), 3.34 (m, 1H), 4.04 (m, 2H), 4.16 (m, 3H), 6.65 (m, 3H), 6.83 (m, 7H), 7.09 (d, J=8.3 Hz, 2H).

EXAMPLE 10

5-[2-[(2,3-Dihydro-1,4-benzoxazin-4-ylmethyl)benzofuran-5-yl]methylene]thiazolidine-2,4-dione

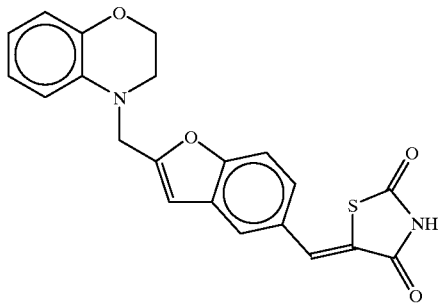

The title compound (2.3 g, 83%) was prepared as a pale yellow solid from 5-formyl-2-(2,3-dihydro-1,4-benzoxazin-4-ylmethyl)benzofuran (2.1 g, 7.17 mmol) obtained in preparation 5 and 2,4-thiazolidinedione (0.838 g, 7.167 mmol) by an analogous procedure to that described in example 1. mp 242–244° C.

$^1$H NMR (DMSO-D$_6$, 200 MHz): δ3.52 (bs, 2H), 4.24 (bs, 2H), 4.71 (s, 2H), 6.57 (m, 1H), 6.76 (m, 2H), 6.93 (m, 2H), 7.56 (d, J=8.72 Hz, 1H), 7.73 (d, J=8.71 Hz, 1H), 7.86 (s, 1H), 7.90 (s, 1H), 12.60 (bs, 1H, D$_2$O exchangeable).

EXAMPLE 11

5-[2-[(2,3-Dihydro-1,4-benzoxazin-4-ylmethyl)benzofuran-5-yl]methyl]thiazolidine-2,4-dione

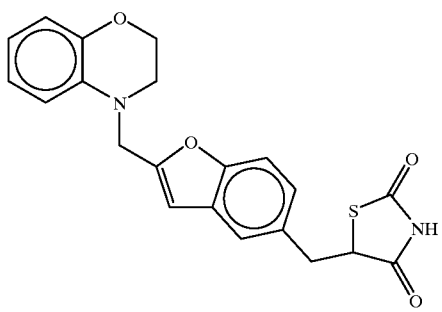

The title compound (1.1 g, 65%) was prepared as a syrupy liquid from 5-[2-[(2,3-dihydro-1,4-benzoxazin-4-ylmethyl)benzofuran-5-yl]methylene]thiazolidine-2,4-dione (1.7 g, 4.33 mmol) obtained in example 10 by a similar manner to that described in example 2.

$^1$H NMR (CDCl$_3$, 200 MHz): δ3.20 (dd, J=14.11 and 9.5 Hz, 1H), 3.56 (m, 3H), 4.30 (t, J=4.25 Hz, 2H), 4.55 (m, 3H), 6.55 (s, 1H), 6.70 (m, 1H), 6.83 (m, 3H), 7.09 (d, J=6.7 Hz, 1H), 7.41 (m, 2H), 8.35 (bs, 1H, D$_2$O exchangeable).

EXAMPLE 12

5-[2-[(2,3-Dihydro-1,4-benzoxazin-4-ylmethyl)benzofuran-5-yl]methyl]thiazolidine-2,4-dione, sodium salt

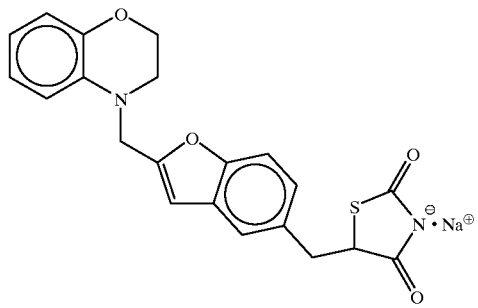

The title compound (0.25 g, 79%) was prepared as a white solid from 5-[2-[(2,3-dihydro-1,4-benzoxazin-4-ylmethyl)benzofuran-5-yl]methyl]thiazolidine-2,4-dione (0.3 g, 0.761 mmol) obtained in example 11 by an analogous procedure to that described in example 3. mp: 299–301° C.

$^1$H NMR (DMSO-d$_6$, 200 MHz): δ2.73 (dd, J=13.7 and 10.7 Hz, 1H), 3.44 (m, 3H), 4.16 (m, 3H), 4.62 (s, 2H), 6.57 (m, 1H), 6.75 (m, 3H), 6.88 (d, J=7.47 Hz, 1H), 7.08 (d, J=9.5 Hz, 1H), 7.36 (s, 1H), 7.40 (s, 1H).

EXAMPLE 13

5-[2-[(Phenothiazin-10-ylmethyl)-benzofuran-5-yl]methylene]thiazolidine-2,4-dione

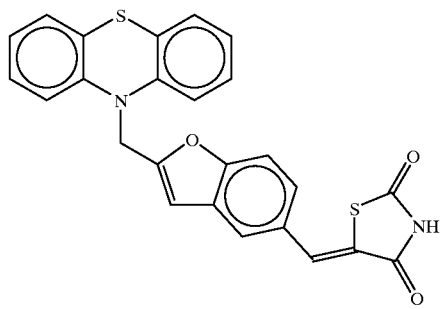

The title compound (1.7 g, 89%) was prepared as a pale yellow solid from 5-formyl-2-[phenothiazin-10-ylmethyl]benzofuran (1.5 g, 4.0 mmol) obtained in preparation 6 by a similar manner to that described in example 1. mp: 199° C.

$^1$H NMR (CDCl$_3$, 200 MHz): δ5.18 (s, 2H), 6.63 (s, 1H), 6.79 (d, J=8.9 Hz, 2H), 7.14 (m, 6H), 7.42 (d, J=8.72 Hz, 1H), 7.58 (d, J=9.0 Hz, 2H), 7.93 (s, 1H).

EXAMPLE 14

5-[2-[(Phenothiazin-10-ylmethyl)benzofuran-5-yl]methyl]thiazolidine-2,4-dione

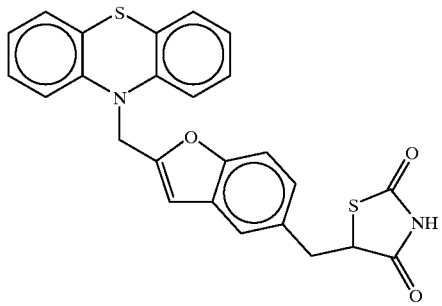

The title compound (0.5 g, 42%) was prepared as a fluffy solid from 5-[2-[(phenothiazin-10-ylmethyl)benzofuran-5-yl]methylene]thiazolidine-2,4-dione (1.2 g, 2.6 mmol) obtained in example 13 by an analogous procedure to that described in example 2. mp: 97–99° C.

$^1$H NMR (CDCl$_3$, 200 MHz): δ3.23 (dd, J=14.11 and 9.55 Hz, 1H), 3.59 (dd, J=14.12 and 4.0 Hz, 1H), 4.56 (dd, J=9.55 and 3.9 Hz, 1H), 5.15 (s, 2H), 6.52 (s, 1H), 6.87 (m, 4H), 7.13 (m, 4H), 7.27 (m, 2H), 7.45 (d, J=8.31 Hz, 1H), 7.92 (bs, 1H, D$_2$O exchangeable).

EXAMPLE 15

5-[4-[2-(Phenothiazin-10-yl)ethoxy]phenyl methylene]thiazolidine-2,4-dione

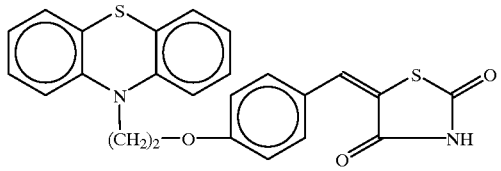

The title compound (5.3 g, 83%) was prepared as an yellow solid from 4-[2-(phenothiazin-10-yl)ethoxy]benzaldehyde (5 g, 14.4 mmol) obtained in preparation 4 by a similar procedure to that described in example 1. mp: 168–170° C.

$^1$H NMR (CDCl$_3$, 200 MHz): δ4.35 (s, 4H), 6.85–7.5 (complex, 12H), 7.8 (s, 1H), 8.9 (bs, 1H, D$_2$O exchangeable).

EXAMPLE 16

5-[4-[2-(Phenothiazin-10-yl)ethoxy]phenyl methylene]thiazolidine-2,4-dione hydrochloride

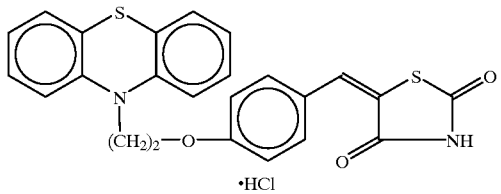

To a solution of 5-[4-[2-(phenothiazin-10-yl)ethoxy]phenyl methylene]thiazolidine-2,4-dione (0.25 g, 0.56 mmol), obtained in example 15 in dry ether (15 mL), HCl gas was passed at 0° C. for 30 min. The resulting solid was filtered and dried to get (0.1 g, 39%) the title compound as brown color solid. mp: 116–118° C.

$^1$H NMR (CDCl$_3$, 200 MHz): δ4.36 (s, 4H), 6.84–7.55 (complex, 12 H), 7.79 (s, 1H), 8.4 (bs, 1H, D$_2$O exchangeable).

EXAMPLE 17

5-[4-[2-(Phenothiazin-10-yl)ethoxy]phenyl methyl]thiazolidine-2,4-dione

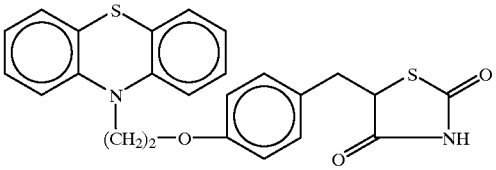

The title compound (2.0 g, 50%) was prepared as a brown color solid from 5-[4-[2-(phenothiazin-10-yl)ethoxy]phenyl methylene]thiazolidine-2,4-dione, obtained in example 15, by an analogous procedure to that described in example 2. mp: 68–70° C.

$^1$H NMR (CDCl$_3$, 200 MHz): δ3.1 (dd, J=14.2 and 9.6 Hz, 1H), 3.45 (dd, J=14.0 and 3.8 Hz, 1H), 4.32 (s, 4H), 4.5 (dd, J=9.2 and 4.0 Hz, 1H), 6.7–7.25 (m, 12 H).

EXAMPLE 18

5-[4-[2-(Phenothiazin-10-yl)ethoxy]phenyl methyl]thiazolidine-2,4-dione, hydrochloride

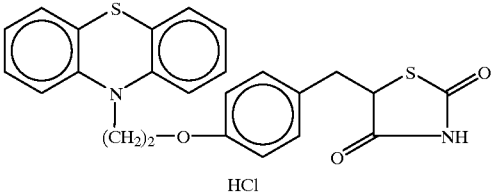

The title compound (0.76 g, 36%) was prepared as a dark brown color solid from 5-[4-[2-(phenothiazin-10-yl)ethoxy]phenyl methyl]thiazolidine-2,4-dione (2.0 g) obtained in example 17, by an analogous procedure to that decribed in example 16. mp: 102° C.

$^1$H NMR (DMSO-d$_6$, 200 MHz): δ2.95–3.45 (m, 2H), 4.27 (s, 4H), 4.85 (dd, J=9.0 and 4.4 Hz, 1H), 6.75–7.4 (m, 12H), 12.0 (s, 1H, D$_2$O exchangeable).

EXAMPLE 19

5-[4-(2-(Phenothiazin-10-yl)ethoxy]phenyl methyl]thiazolidine-2,4-dione, sodium salt

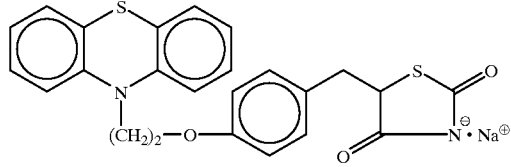

The title compound (0.26 g, 71%) was prepared as a white solid from 5-[4-[2-(phenothiazin-10-yl)ethoxy]phenyl methyl]thiazolidine-2,4-dione (0.35 g), obtained in example 17, by an analogous procedure to that described in example 3. mp: 206–208° C.

¹H NMR (DMSO-d₆, 200 MHz): δ2.6 (m, 1H), 3.3 (m, 1H), 4.05 (dd, J=10.6 and 3.2 Hz, 1H), 4.27 (s, 4H), 6.7–7.3 (m, 12 H).

EXAMPLE 20

5-[4-[2-(Phenothiazin-10-yl)ethoxy]3-methoxyphenyl methylene]thiazolidine-2,4-dione

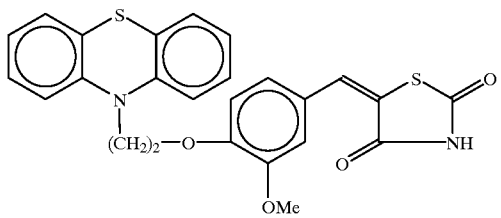

The title compound (0.8 g, 67%) was prepared as yellow solid from 4-[2-[phenothiazin-10-yl)ethoxy]-3-methoxy benzaldehyde (1.0 g), obtained in preparation 7, by a similar procedure to that described in example 1. mp: 210–212° C.

¹H NMR (CDCl₃, 200 MHz): δ3.92 (s, 3H), 4.41 (s, 4H), 6.8–7.4 (m, 11H), 7.72 (s, 1H).

EXAMPLE 21

5-[4-[2-(Phenothiazin-10-yl)ethoxy]-3-methoxyphenyl methyl]thiazolidine-2,4-dione

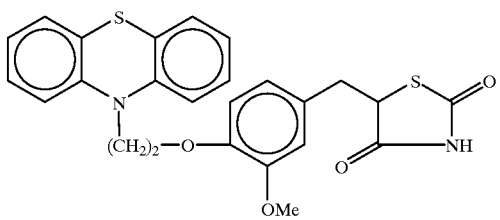

The title compound (0.35 g, 66%) was prepared as a brown color solid from 5-[4-[2-(phenothiazin-10-yl)ethoxy]-3-methoxyphenyl methylene]thiazolidine-2,4-dione (0.5 g) obtained in example 20, by an analogous procedure to that described in example 2, mp: 46–48° C.

¹H NMR (CDCl₃, 200 MHz): δ3.08 (m, 1H), 3.45 (dd, J=14.2 and 3.6 Hz, 1H), 3.86 (s, 3H), 4.35 (s, 4H), 4.5 (dd, J=9.6 and 3.8 Hz, 1H), 6.65–7.35 (m, 1H).

EXAMPLE 22

5-[4-[2-[Phenoxazin-10-yl]ethoxy]phenyl methylene]-4-oxazolidinone-2-thione

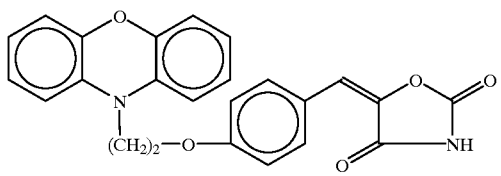

A solution of 4-[2-(phenoxazin-10-yl)ethoxy]benzaldehyde (0.3 g, 0.9 mmol) obtained in preparation 3 and 4-oxazolidinone-2-thione (0.13 g, 1 mmol) in acetic acid (5 mL) containing sodium acetate (0.23 g, 2.7 mmol) was heated at reflux for 5 h. The reaction mixture was cooled and poured into ice water. The resulting solid was filtered and washed with water and dried to get (0.3 g, 61%) the title compound as an orange color solid. mp: 184–186° C.

¹H NMR (CDCl₃, 200 MHz): δ4.0 (t, J=6.4 Hz, 2H), 4.25 (t, J=6.4 Hz, 2H), 6.5–7.1 (m, 10 H), 7.37 (s, 1H), 7.78 (d, J=8.8 Hz, 2H).

EXAMPLE 23

5-[4-(2-(9-Oxophenothiazin-10-yl)ethoxy]phenyl methylene]thiazolidine-2,4-dione

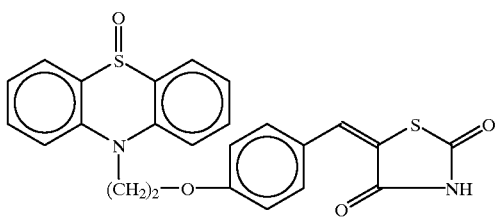

The title compound (1.0 g, 57%) was prepared as a pale yellow solid from 4-[2-(9-oxophenothiazin-10-yl)ethoxy] benzaldehyde (1.4 g, 3.8 mmol), obtained in preparation 8, by a similar procedure to that described in example 1. mp: 262–264° C.

¹H NMR (DMSO-d₆, 200 MHz): δ4.5 (m, 2H), 4.81 (m, 2H), 7.12 (d, J=8.6 Hz, 2H), 7.32 (t, J=7.0 Hz, 2H), 7.54 (d, J=8.6 Hz, 2H), 7.8 (m, 5H), 7.98 (d, J=7.4 Hz, 2H), 12.53 (bs, 1H, D₂O exchangeable).

EXAMPLE 24

5-[4-[2-(9,9-Dioxophenothiazin-10-yl)ethoxy]phenyl methylene]thiazolidine-2,4-dione

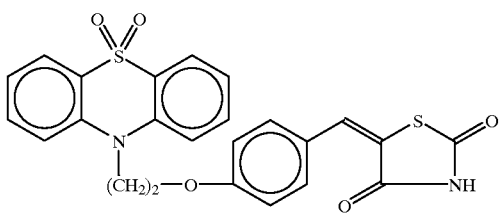

The title compound (0.14 g, 56%) was prepared as a dark brown color solid from 4-[2-(9,9-dioxophenothiazin-10-yl] ethoxy]benzaldehyde (0.2 g, 0.53 mmol), obtained in preparation 9, by a similar procedure to that described in example 1. mp: 248–250° C.

¹H NMR (DMSO-d₆, 200 MHz) δ: 4.49 (bs, 2H), 4.79 (bs, 2H), 7.06 (d, J=8.4 Hz, 2H), 7.38 (t, J=5.8 Hz, 2H), 7.52 (d, J=8.2 Hz, 2H), 7.7 (s, 1H), 7.79 (s, 4H), 8.01 (d, J=7.6 Hz, 2H), 12.5 (bs, 1H, D₂O exchangeable).

EXAMPLE 25

5-[4-[2-[2-Trifluoromethyl-phenothiazin-10-yl]ethoxy]phenyl methylene]thiazolidine-2,4-dione

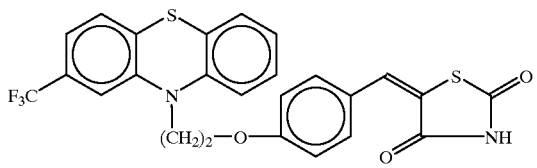

The title compound (1.7 g, 71%) was prepared as a pale yellow solid from 4-[2-[2-trifluoromethyl phenothiazin-10-yl]ethoxy]benzaldehyde (1.9 g, 4.7 mmol) obtained in preparation 10, by a similar procedure to that described in example 1. mp: 196–198° C.

$^1$H NMR (DMSO-d$_6$, 200 MHz): δ4.39 (s, 4H), 6.9–7.6 (m, 11H), 7.72 (s, 1H), 12.5 (bs, 1H, D$_2$O exchangeable).

EXAMPLE 26

5-[4-[2-[2-Trifluoromethylphenothiazin-10-yl]ethoxy]phenyl methyl]thiazolidine-2,4-dione

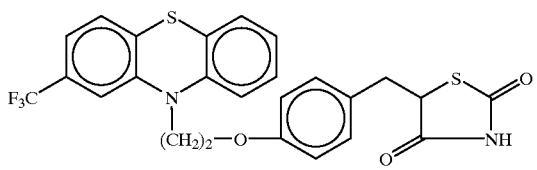

The title compound (0.2 g, 30%) was prepared as a pale yellow solid from 5-[4-[2-[2-trifluoromethylphenothiazin-10-yl]ethoxy]phenyl methylene]thiazolidine-2,4-dione (0.68 g, 1.3 mmol) obtained in example 25 by an analogous procedure to that described in example 2. mp: 64° C.

$^1$H NMR (CDCl$_3$, 200 MHz): δ3.1 (dd, J=14.2 and 9.4 Hz, 1H), 3.44 (dd, J=14.2 and 4.0 Hz, 1H), 4.31 (s, 4H), 4.5 (dd, J=9.4 and 4.0 Hz, 1H), 6.7–7.3 (m, 11H)

Mutation in colonies of laboratory animals and different sensitivities to dietary regimens have made the development of animal models with non-insulin dependent diabetes associated with obesity and insulin resistance possible. Genetic models such as db/db and ob/ob (See Diabetes, (1982) 31(1): 1–6) in mice and fa/fa and zucker rats have been developed by the various laboratories for understanding the pathophysiology of disease and testing the efficacy of new antidiabetic compounds (Diabetes, (1983) 32: 830–838; Annu. Rep. Sankyo Res. Lab. (1994). 46: 1–57). The homozygous animals, C57 BL/KsJ-db/db mice developed by Jackson Laboratory, US, are obese, hyperglycemic, hyperinsulinemic and insulin resistant (J. Clin. Invest., (1990) 85: 962–967), whereas heterozygous are lean and normoglycemic. In db/db model, mouse progressively develops insulinopenia with age, a feature commonly observed in late stages of human type II diabetes when blood sugar levels are insufficiently controlled. The state of pancreas and its course vary according to the models. Since this model resembles that of type II diabetes mellitus, the compounds of the present invention were tested for blood sugar and triglycerides lowering activities.

The compounds of the present inventions showed blood sugar and triglycerides lowering activities through improved insulin resistance. This was demonstrated by the following in vivo experiments.

Male C57BL/KsJ-db/db mice of 8 to 14 weeks age, having body weight range of 35 to 60 grams, procured from the Jackson Laboratory, USA, were used in the experiment. The mice were provided with standard feed (National Institute of Nutrition, Hyderabad, India) and acidified water, ad libitum. The animals having more than 300 mg/dl blood sugar were used for testing. The number of animals in each group was 4.

The random blood sugar and triglyceride levels were measured by collecting blood (100 μl) through orbital sinus, using heparinised capillary in tubes containing EDTA which was centrifuged to obtain plasma. The plasma glucose and triglyceride levels were measured spectrometrically, by glucose oxidase and glycerol-3-PO$_4$ oxidase/peroxidase enzyme (Dr. Reddy's Lab. Diagnostic Division Kits, Hyderabad, India) methods respectively. On 6th day the blood samples were collected one hour after administration of test compounds/vehicle for assessing the biological activity.

Test compounds were suspended on 0.25% carboxymethyl cellulose and administered to test group at a dose of 10 mg to 200 mg/kg through oral gavage daily for 6 days. The control group received vehicle (dose 10 ml/kg). Troglitazone (100 mg/kg, daily dose) was used as a standard drug which showed 28% reduction in random blood sugar level on 6th day.

The blood sugar and triglycerides lowering activities of the test compound was calculated according to the formula:

$$\text{Blood sugar/ triglycerides lowering activity (\%)} = 1 - \frac{DT/DC}{TC/ZC} \times 100$$

ZC=Zero day control group value
DC=Zero day treated group value
TC=Control group value on test day
DT=Treated group value on the test day No adverse effects were observed for any of the mentioned compounds of invention in the above test.

| Compound | Dose (mg/kg) | Reduction in Blood Glucose Level (%) | Triglyceride Lowering (%) |
|---|---|---|---|
| Example 19 | 10 | 43 | 26 |
| Example 6 | 30 | 49 | 46 |
| Example 3 | 30 | 62 | 55 |

The experimental results from the db/db mice suggest that the novel compounds of the present invention also possess therapeutic utility as a prophylactic or regular treatment for obesity, cardiovascular disorders such as hypertension, hyperlipidaemia and other diseases; as it is known from the literature that such diseases are interrelated to each other.

Blood glucose level and triglycerides are also lowered at doses greater than 30 mg/kg. Normally, the quantum of reduction is dose dependent.

What is claimed is:

1. A compound of formula (I)

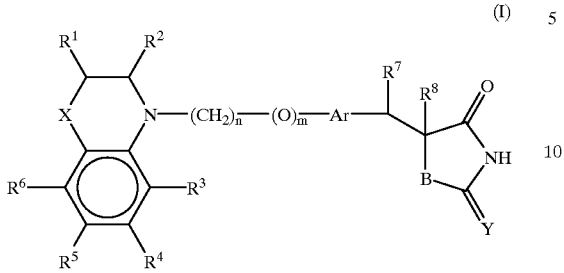

its tautomeric forms, its stereoisomers, its polymorphs, its pharmaceutically acceptable salts or its pharmaceutically acceptable solvates, wherein $R^3$, $R^4$, $R^5$, and $R^6$ are the same or different and represent hydrogen, halogen, hydroxy, cyano, nitro or optionally substituted groups selected from alkyl, $(C_3-C_6)$cycloalkyl, alkoxy, $(C_3-C_6)$cycloalkoxy, aryl, aryloxy, aralkyl, aralkoxy; heterocyclyl selected from aziridinyl, pyrrolidinyl, morpholinyl, piperidinyl, or piperazinyl; heteroaryl, heteroaralkyl, heteroaryloxy, heteroaralkoxy, acyl, acyloxy, hydroxyalkyl, amino, acylamino, aralkylamino, aminoalkyl, arylamino, alkoxycarbonyl, aryloxycarbonyl, aralkoxycarbonyl, alkylamino, alkoxyalkyl, aryloxyalkyl, alkylmercapto, aralkoxycarbonylamino, alkoxycarbonylamino, aryloxycarbonylamino, mercaptoalkyl groups, carboxylic acid or its derivatives, or sulfonic acid or its derivatives; $R^1$ and $R^2$ together represent along with carbon atoms to which they are attached an aromatic cyclic structure containing 5–6 ring atoms which may optionally be substituted; X represents a heteroatom selected from oxygen or sulfur; Ar represents an optionally substituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl or pyrazolyl; $R^7$ represents hydrogen atom, hydroxy, alkoxy, halogen, lower alkyl group or optionally substituted aralkyl group or forms a bond together with $R^8$; $R^8$ represents hydrogen atom, hydroxy, alkoxy, halogen, lower alkyl group or optionally substituted aralkyl or $R^8$ forms a bond together with $R^7$; B represents an oxygen atom or a sulfur atom; Y represents an oxygen atom or a sulfur atom, n is an integer ranging from 1 to 4 and m is an integer of zero or one.

2. A compound as claimed in claim 1, wherein $R^1$ and $R^2$ together with the adjacent carbon atoms to which they are attached represent an optionally substituted 5 to 6 membered aromatic ring structure having 5 to 6 ring atoms wherein when the aromatic ring structure is substituted the substituents are selected from halogen, $(C_1-C_6)$alkoxy, cyclo $(C_3-C_6)$alkyl, cyclo$(C_3-C_6)$alkoxy, aryl, aralkyl, aralkoxy, heterocyclyl, hydroxy, acyl, acyloxy, carboxyl, alkoxycarbonyl, aralkoxycarbonyl, amino, alkylamino, acylamino, aralkoxy, carbonylamino, and aminocarbonyl.

3. An intermediate of formula (III)

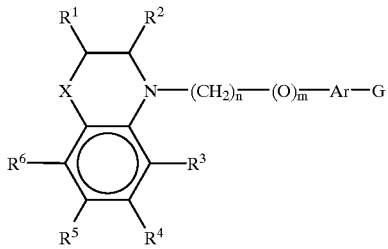

wherein G represents —CHO, —NO$_2$, —NH$_2$ or —CH$_2$CH(J)—COOR, where J represents halogen atom and R represents hydrogen or $(C_1-C_6)$alkyl group; $R^3$, $R^4$, $R^5$, and $R^6$ are the same or different and represent hydrogen, halogen, hydroxy, cyano, nitro or optionally substituted groups selected from alkyl, $(C_3-C_6)$cycloalkyl, alkoxy, $(C_3-C_6)$cycloalkoxy, aryl, aryloxy, aralkyl, aralkoxy, heterocyclyl selected from aziridinyl, pyrrolidinyl, morpholinyl, piperidinyl, or piperazinyl; heteroaryl, heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkoxycarbonyl, aralkoxycarbonylamino, alkoxycarbonylamino, aryloxycarbonylamino, alkylamino, alkoxyalkyl, aryloxyalkyl, alkylmercapto, mercaptoalkyl groups, carboxylic acid or its derivatives, or sulfonic acid or its derivatives; $R^1$ and $R^2$ together represent along with carbon atoms to which they are attached an aromatic cyclic structure containing 5–6 ring atoms which may optionally be substituted with halogen, $(C_1-C_6)$alkoxy, cyclo$(C_3-C_6)$alkyl, cyclo$(C_3-C_6)$alkoxy, aryl, aralkyl, aralkoxy, heterocyclyl, hydroxy, acyl, acyloxy, carboxyl, alkoxycarbonyl, aralkoxycarbonyl, amino, alkylamino, acylamino, aralkoxycarbonylamino, or aminocarbonyl; X represents a heteroatom selected from oxygen, or sulfur; Ar represents an optionally substituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl or pyrazolyl; n is an integer ranging from 1 to 4 and m is an integer of zero or 1 with the proviso that when X represents sulfur, n is 1 and m is 0, G does not represent NO$_2$.

4. An intermediate of formula III

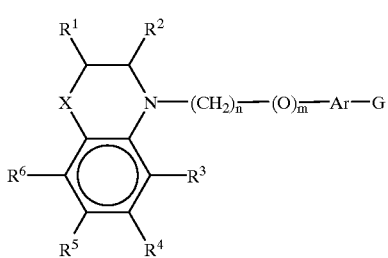

where $R^1$–$R^6$, X, n, m, Ar and G are as defined in claim 3, with the proviso that when X represents sulfur, n is 1 and m is 0, G does not represent NO$_2$ prepared by the process which comprises the steps of:

a) reacting of the compound of the formula (IV),

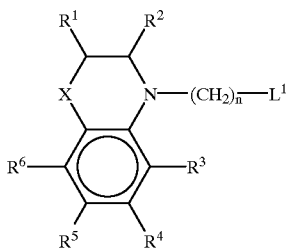
(IV)

wherein, $R^1$–$R^6$, X, and n are as defined in claim 3 and $L^1$ is a halogen atom or a leaving group with a compound of formula (V)

HO—Ar—G  (V)

where G is a CHO or a $NO_2$ group and Ar is as defined in claim 3; or b) reacting a compound of formula (VI)

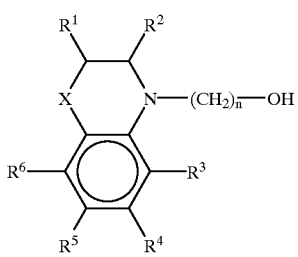
(VI)

where $R^1$–$R^6$, X and n are as defined in claim 3, with a compound of formula (VII)

$L^2$—Ar—G  (VII)

where G is a CHO or $NO_2$ group and Ar is as defined in claim 3 and $L^2$ represents a halogen atom or;

c) reacting a compound of formula (VI)

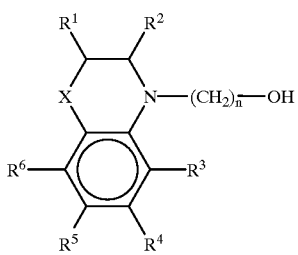
(VI)

where $R^1$–$R^6$, X and n are as defined in claim 3, with a compound of formula (V)

HO—Ar—G  (V)

where G is a CHO or a $NO_2$ group and Ar is as defined in claim 3;

d) reacting a compound of formula (VIII)

$L^1$—$(CH_2)_n$—$(O)_m$—Ar—G  (VIII)

where $L^1$ is a halogen atom or a leaving group; n, m and Ar are as defined in claim 3, and G is a CHO or $NO_2$ group with a compound of formula (IX)

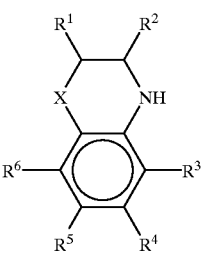
(IX)

where $R^1$–$R^6$ and X are as defined in claim 3.

5. A process for the preparation of a compound of formula (I)

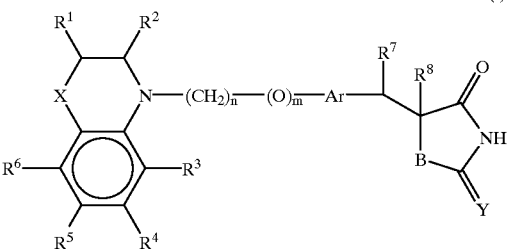
(I)

its tautomeric forms, its stereoisomers, its polymorphs, its pharmaceutically acceptable salts or its pharmaceutically acceptable solvates, wherein $R^3$, $R^4$, $R^5$, and $R^6$ are the same or different and represent hydrogen, halogen, hydroxy, cyano, nitro or optionally substituted groups selected from alkyl, $(C_3$–$C_6)$cycloalkyl, alkoxy, $(C_3$–$C_6)$cycloalkoxy, aryl, aryloxy, aralkyl, aralkoxy, heterocyclyl selected from aziridinyl, pyrrolidinyl, morpholinyl, piperidinyl or piperazinyl; heteroaryl, heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkoxycarbonyl, alkylamino, alkoxyalkyl, aryloxyalkyl, alkylmercapto, aralkoxycarbonylamino, alkoxycarbonylamino, aryloxycarbonylamino, mercaptoalkyl groups, carboxylic acid or its derivatives, or sulfonic acid or its derivatives; $R^1$ and $R^2$ together represent along with carbon atoms to which they are attached an aromatic cyclic structure containing 5–6 ring atoms which may optionally be substituted; X represents a heteroatom selected from oxygen or sulfur; Ar represents an optionally substituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl or pyrazolyl: $R^7$ represents hydrogen atom, hydroxy, alkoxy, halogen, lower alkyl group or optionally substituted aralkyl group or forms a bond together with $R^8$; $R^8$ represents hydrogen atom, hydroxy, alkoxy, halogen, lower alkyl group or optionally substituted aralkyl or $R^8$ forms a bond together with $R^7$; B represents an oxygen atom or a sulfur atom; Y represents an oxygen atom or a sulfur atom, n is an integer ranging from 1 to 4 and m is an integer of zero or one, which comprises:

a) reacting the intermediate of formula (III),

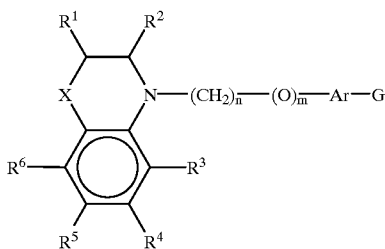

(III)

wherein G represents —CHO, —NO$_2$, —NH$_2$, or CH$_2$CH(J)—COOR, where J represents halogen atom and R represents hydrogen or (C$_1$–C$_6$) alkyl group and R$^1$, R$^2$, R$^3$, R$^4$, R$^5$, R$^6$, X, n, m, and Ar are as defined above, with 2,4-thiazolidinedione, 2,4-oxazolidinedione or oxazolidine-4-oxo-2-thione to obtain a compound of formula (X)

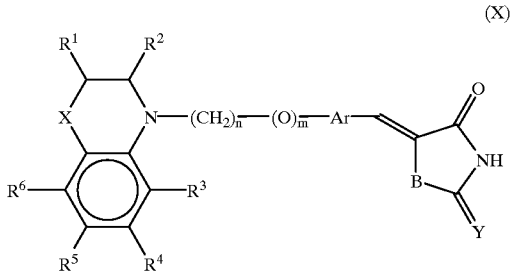

(X)

where R$^1$–R$^6$, X, Ar, n, m, B and Y are as defined above and, R$^7$ and R$^8$ together represent a bond; if needed, b) reducing the compound of formula (X) obtained in step (i), to obtain the compound of formula (XI)

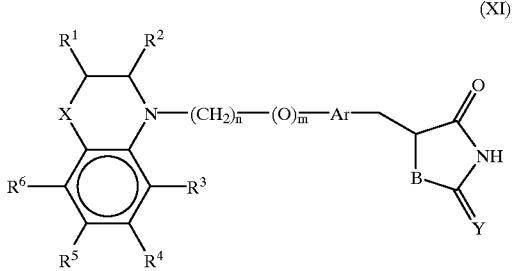

(XI)

where R$^1$–R$^6$, X, Ar, n, m, B and Y are as defined above and if needed, c) converting the compounds of formula (X) and of formula (XI) obtained above into pharmaceutically acceptable salts, or pharmaceutically acceptable solvates.

6. A compound according to claim 1, which is selected from the group consisting of the following compounds:

5-[4-[2-(Phenoxazin-10-yl)ethoxy]phenyl methylene] thiazolidine-2,4-dione;
5-[4-[2-(Phenoxazin-10-yl)ethoxy]phenyl methyl] thiazolidine-2,4-dione;
5-[4-[2-(Phenoxazin-10-yl)ethoxy]phenyl methyl] thiazolidine-2,4-dione, sodium salt;
5-[2-[(Phenothiazin-10-ylmethyl)-benzofuran-5-yl] methylene]thiazolidine-2,4-dione;
5-[2-[(Phenothiazin-10-ylmethyl)benzofuran-5-yl]methyl] thiazolidine-2,4-dione;
5-[4-[2-(Phenothiazin-10-yl)ethoxy]phenyl methylene] thiazolidine-2,4-dione;
5-[4-[2-(Phenothiazin-10-yl)ethoxy]phenyl methylene] thiazolidine-2,4-dione hydrochloride;
5-[4-[2-(Phenothiazin-10-yl)ethoxy]phenyl methyl] thiazolidine-2,4-dione;
5-[4-[2-(Phenothiazin-10-yl)ethoxy]phenyl methyl] thiazolidine-2,4-dione, hydrochloride;
5-[4-(2-(Phenothiazin-10-yl)ethoxy]phenyl methyl] thiazolidine-2,4-dione, sodium salt;
5-[4-[2-(Phenothiazin-10-yl)ethoxy]-3-methoxyphenyl methylene]thiazolidine-2,4-dione;
5-[4-[2-(Phenothiazin-10-yl)ethoxy]-3-methoxyphenyl methyl]thiazolidine-2,4-dione;
5-[4-[2-[Phenoxazin-10-yl]ethoxy]phenyl methylene]-4-oxazolidinone-2-thione;
5-[4-[2-(9-Oxophenothiazin-10-yl)ethoxy]phenyl methylene]thiazolidine-2,4-dione;
5-[4-[2-(9,9-Dioxophenothiazin-10-yl)ethoxy]phenyl methylene]thiazolidine-2,4-dione;
5-[4-[2-[2-Trifluoromethylphenothiazin-10-yl]ethoxy] phenyl methylene]thiazolidine-2,4-dione; and
5-[4-[2-[2-Trifluoromethylphenothiazin-10-yl]ethoxy] phenyl methyl]thiazolidine-2,4-dione.

7. A composition which comprises a compound of formula (I)

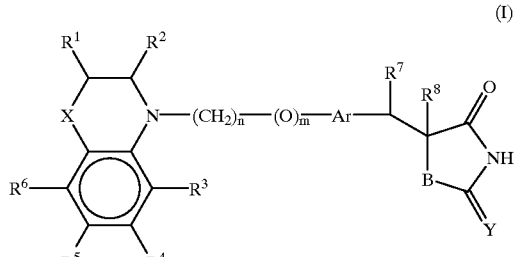

(I)

as defined in claim 1, and a pharmaceutically acceptable carrier, diluent, excipient or solvate.

8. A composition as claimed in claim 7, in the form of a tablet, capsule, powder, syrup, solution or suspension.

9. A pharmaceutical composition which comprises a compound according to claim 6, and a phamaceutically acceptable carrier, diluent, solvate or excipient.

10. A composition as claimed in claim 9 in the form of a tablet, capsule, powder, syrup, solution or suspension.

11. A compound of formula (I)

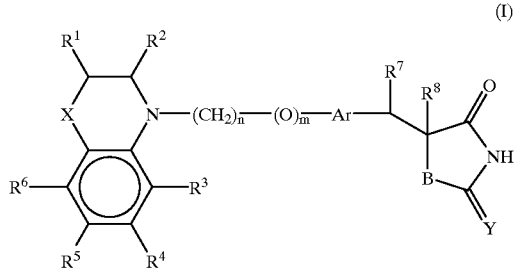

(I)

its tautomeric forms, its stereoisomers, its polymorphs, its pharmaceutically acceptable salts or its pharmaceutically acceptable solvates, wherein R$^3$, R$^4$, R$^5$, and R$^6$ are the same or different and represent hydrogen, halogen, hydroxy, cyano, nitro or optionally substituted groups selected from alkyl, $(C_3-C_6)$cycloalkyl, alkoxy, $(C_3-C_6)$cycloalkoxy, aryl, aryloxy, aralkyl, aralkoxy; heterocyclyl selected from aziridinyl, pyrrolidinyl, morpholinyl, piperidinyl, or piperazinyl; heteroaryl, heteroaralkyl, heteroaryloxy, heteroaralkoxy, acyl, acyloxy, hydroxyalkyl, amino, acylamino, arylamino, aralkylamino, aminoalkyl, alkoxycarbonyl, aryloxycarbonyl, aralkoxycarbonyl, alkylamino, alkoxyalkyl, aryloxyalkyl, alkylmercapto, aralkoxycarbonylamino, alkoxycarbonylamino, aryloxycarbonylamino, mercaptoalkyl groups, carboxylic acid or its derivatives, or sulfonic acid or its derivatives; $R^1$ and $R^2$ together represent along with carbon atoms to which they are attached an aromatic cyclic structure containing 5–6 ring atoms which may optionally be substituted; X represents a heteroatom selected from oxygen or sulfur; Ar represents an optionally substituted divalent phenylene, naphthylene, pyridyl, quinolinyl, benzofuranyl, benzoxazolyl, benzothiazolyl, indolyl, indolinyl, azaindolyl, azaindolinyl, indenyl, dihydrobenzofuryl, benzopyranyl, dihydrobenzopyranyl or pyrazolyl; $R^7$ represents hydrogen atom, hydroxy, alkoxy, halogen, lower alkyl group or optionally substituted aralkyl group or forms a bond together with $R^8$; $R^8$ represents hydrogen atom, hydroxy, alkoxy, halogen, lower alkyl group or optionally substituted aralkyl or $R^8$ forms a bond together with $R^7$; B represents an oxygen atom or a sulfur atom; Y represents an oxygen atom or a sulfur atom, n is an integer ranging from 1 to 4 and m is an integer of zero or one prepared according to the process of claim 5.

12. A method of preventing or treating diabetes caused by insulin resistance or impaired glucose tolerance or complications of diabetes caused by insulin resistance or impaired glucose tolerance comprising administering a therapeutically effective amount of a compound of formula (I) as defined in claim 1, and a pharmaceutically acceptable carrier, diluent, excipient or solvate to a patient in need thereof.

13. The method according to claim 12, wherein the complication is hyperlipemia, hypercholesteremia, hyperglycemia, dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephritis, glomerular sclerosis, nephrotic syndrome, hypertensive nephrosclerosis, end-stage renal disease, microalbuminuria or eating disorder.

14. A method of reducing blood glucose, triglycerides or free fatty acids in a patient in need thereof comprising administering a therapeutically effective amount of a compound of formula (I), as defined in claim 1, and a pharmaceutically acceptable carrier, diluent, excipient or solvate.

15. A method of preventing or treating diabetes caused by insulin resistance or impaired glucose tolerance or complications of diabetes said diabetes caused by insulin resistance or impaired glucose tolerance comprising administering a therapeutically effective amount of a compound of formula (I) as defined in claim 6, and a pharmaceutically acceptable carrier, diluent, solvate or excipient to a patient in need thereof.

16. A method according to claim 15, wherein the complication is hyperlipemia, hypercholestermia, hyperglycemia, dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephritis, glomerular sclerosis, nephrotic syndrome, hypertensive nephrosclerosis, end-stage renal disease, microalbuminuria or eating disorders.

17. A method of reducing blood glucose, triglycerides or free fatty acids in a patient in need thereof comprising administering a therapeutically effective amount of a compound of formula (I), as defined in claim 6 and a pharmaceutically acceptable carrier, diluent, excipient or solvate.

18. 5-[4-[2-(Phenothiazin-1-yl)ethoxy]phenyl methyl] thiazolidine-2,4-dione of the formula

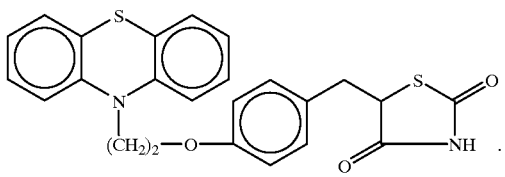

19. A composition which comprises the compound of claim 18, and a pharmaceutically acceptable carrier, diluent, excipient or solvate.

20. A composition as claimed in claim 19, in the form of a tablet, capsule, powder, syrup, solution or suspension.

21. A method of preventing or treating diabetes caused by insulin resistance or impaired glucose tolerance or complications of diabetes said diabetes caused by insulin resistance or impaired glucose tolerance comprising administering a therapeutically effective amount of a compound of formula (I) as defined in claim 18, and a pharmaceutically acceptable carrier, diluent, solvate or excipient to a patient in need thereof.

22. A method according to claim 21, wherein the complication is hyperlipemia, hypercholesteremia, hyperglycemia, dyslipidaemia, hypertension, coronary heart disease, cardiovascular disorders, atherosclerosis, obesity, psoriasis, polycystic ovarian syndrome (PCOS), renal diseases, diabetic nephropathy, glomerulonephritis, glomerular sclerosis, nephrotic syndrome, hypertensive nephrosclerosis, end-stage renal disease, microalbuminuria or eating disorders.

23. A method of reducing blood glucose, triglycerides or free fatty acids in a patient in need thereof comprising administering a therapeutically effective amount of a compound of formula (I), as defined in claim 18 and a pharmaceutically acceptable carrier, diluent, excipient or solvate.

* * * * *